United States Patent
Buynak

(10) Patent No.: US 10,519,161 B2
(45) Date of Patent: Dec. 31, 2019

(54) METHODS OF GENERATING BETA-LACTAMASE RESISTANT CARBAPENEM COMPOUNDS

(71) Applicant: Southern Methodist University, Dallas, TX (US)

(72) Inventor: John D. Buynak, Dallas, TX (US)

(73) Assignee: Southern Methodist University, Dallas, TX (US)

( * ) Notice: Subject to any disclaimer, the term of this patent is extended or adjusted under 35 U.S.C. 154(b) by 0 days.

(21) Appl. No.: 14/066,367

(22) Filed: Oct. 29, 2013

(65) Prior Publication Data

US 2014/0121192 A1    May 1, 2014

Related U.S. Application Data

(60) Provisional application No. 61/719,817, filed on Oct. 29, 2012.

(51) Int. Cl.
*C07D 477/20* (2006.01)
*A61P 31/00* (2006.01)
*C07D 477/26* (2006.01)

(52) U.S. Cl.
CPC ................................ *C07D 477/26* (2013.01)

(58) Field of Classification Search
CPC .................................................. C07D 477/20
USPC ....................................... 514/210.1; 540/350
See application file for complete search history.

(56) References Cited

U.S. PATENT DOCUMENTS

| | | |
|---|---|---|
| 4,543,257 A | 9/1985 | Cama et al. |
| 4,559,157 A | 12/1985 | Smith et al. |
| 4,608,392 A | 8/1986 | Jacquet et al. |
| 4,775,669 A | 10/1988 | Cama et al. |
| 4,820,508 A | 4/1989 | Wortzman |
| 4,933,333 A * | 6/1990 | Sunagawa ............ C07D 205/08 514/192 |
| 4,938,949 A | 7/1990 | Borch et al. |
| 4,992,478 A | 2/1991 | Geria |
| 5,006,519 A | 4/1991 | Dininno et al. |
| 5,032,587 A | 7/1991 | Dininno et al. |
| 5,258,509 A | 11/1993 | Nakagawa et al. |
| 5,672,701 A * | 9/1997 | Martel et al. ................ 540/350 |
| 6,180,621 B1 | 1/2001 | Kawamoto et al. |
| 6,770,759 B2 | 8/2004 | Buynak et al. |
| 7,022,691 B2 | 4/2006 | Buynak et al. |
| 7,468,364 B2 | 12/2008 | Sunagawa et al. |
| 8,148,520 B2 | 4/2012 | Surulichamy et al. |
| 2009/0312539 A1 | 12/2009 | Gnanaprakasam et al. |
| 2010/0173887 A1 | 7/2010 | Pfaendler |

FOREIGN PATENT DOCUMENTS

| | | |
|---|---|---|
| EP | 0178911 A2 | 4/1986 |
| EP | 0368259 A1 | 5/1990 |
| EP | 0017992 A | 9/1990 |
| EP | 466254 A1 | 3/1991 |
| EP | 466253 A1 | 1/1992 |
| JP | 02223587 A1 | 10/2012 |
| WO | 1996024684 A1 | 8/1996 |
| WO | 2002053566 A1 | 7/2002 |
| WO | 2003040146 A1 | 5/2003 |
| WO | 2003089431 A1 | 10/2003 |
| WO | 2012139414 A1 | 10/2012 |

OTHER PUBLICATIONS

International Search Report and Written Opinion issued by FIPS for PCT/US2013/067313 dated Mar. 13, 2014.

* cited by examiner

*Primary Examiner* — Irina Neagu
(74) *Attorney, Agent, or Firm* — Edwin S. Flores; Chalker Flores, LLP

(57) ABSTRACT

The present invention includes compositions, methods of making and using novel carbapenem compounds including active agents, compounds, antibacterial agents, pharmaceutically acceptable salts of C1α-C1β di-substituted carbapenem compounds, C5α substituted carbapenem compounds, C6α-C6β di-substituted carbapenem compounds and combinations thereof.

2 Claims, 10 Drawing Sheets

METHODS OF GENERATING BETA-LACTAMASE RESISTANT CARBAPENEM COMPOUNDS

CROSS-REFERENCE TO RELATED APPLICATIONS

This application claims priority based on U.S. Provisional Application No. 61/719,817, filed Oct. 29, 2012. The contents of which is incorporated by reference in its entirety.

STATEMENT OF FEDERALLY FUNDED RESEARCH

This invention was made with U.S. Government support under Contract No. 1R41AI102507-01 awarded by the Department of Health and Human Services National Institutes of Health. The government has certain rights in this invention.

TECHNICAL FIELD OF THE INVENTION

The present invention relates generally to carbapenem compounds and more particularly relates to carbapenem compounds having substitutions at the 5 and/or 6 positions of the basic nucleus of the carbapenem compound.

INCORPORATION-BY-REFERENCE OF MATERIALS FILED ON COMPACT DISC

None.

BACKGROUND OF THE INVENTION

Without limiting the scope of the invention, its background is described in connection with carbapenem compounds having substitutions at the 5 position, the 6 position or both the 5 and 6 position of the basic nucleus of the 7-oxo-1-azabicyclo[3,2,0]hept-2-ene carbapenem compound.

An important mechanism of microbial resistance to β-lactam antibiotics is the bacterial production of enzymes that hydrolytically destroy β-lactam antibiotics, e.g., β-lactamases which include penicillins and cephalosporins. The resistance to β-lactam antibiotics can be transferred by plasmids that are capable of rapidly spreading the resistance to other members of the same strain and even other species. As a result of this transfer process, a patient can become infected with multiple organisms each resistance to β-lactam antibiotics. Based on the amino acid sequence β-lactamase enzymes have been organized into four molecular classes: Class A (preferentially hydrolyze penicillins), Class B (metalloenzymes), Class C (chromosomal cephalosporinases) and Class D (exhibit a unique substrate profile).

One strategy for overcoming this bacterial resistance is the use of β-lactamases inhibitors which are commonly administered in conjunction with an antibiotic since β-lactamase inhibitors do not possess antibiotic activity themselves. Current commercial inhibitors historically target only the clinically relevant class A β-lactamases; however, there has been an increase in the number of infections possessing class B, C, and D β-lactamases.

U.S. Patent Application Publication No. 2007/0265242, entitled, "Novel Carbapenem Compound," discloses a carbapenem compound represented by the following formula

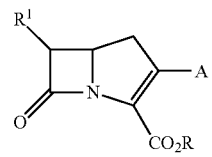

wherein R1 is C1 to C3 alkyl or C1 to C3 alkyl substituted by hydroxy. R is hydrogen atom or a group which regenerates a carboxyl group by hydrolysis in a living body, A is the following formula

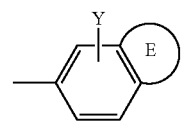

wherein E is a 5 to 7 membered cyclic ring optionally containing 1 to 3 hetero atoms (excluding benzene ring) which forms a bicyclic ring in cooperation with the benzene ring, Y is hydrogen atom, C1 to C4 alkyl, C1 to C4 alkoxy, trifluoromethoxy, halogen atom or cyano group, or its pharmaceutically acceptable salt.

U.S. Pat. No. 7,022,691, entitled, "Inhibitors of Serine and Metallo-β-Lactamases" discloses compounds of the following formula:

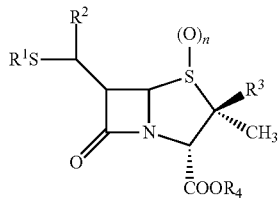

useful for inhibiting simultaneously serine and metallo-β-lactamases enzymes, for enhancing the activity of β-lactam antibiotics, and for treating β-lactam resistant bacterial infections in a mammal.

U.S. Pat. No. 6,770,759, entitled, "Penicillanic Acid Derivative Compounds and Methods of Making," discloses carbapenem compounds which have been developed and commercialized are poor in absorbability from the digestive tract, and; therefore, they are clinically used only in the form of injection, mainly intravenous injection. However, in the clinical field, it is desirable to select several administration routes from the viewpoint of circumstances or wishes of a patient, a therapeutic object, etc. Especially, oral administration of an antibacterial agent is easy and convenient for administration to a patient in comparison with injection. In view of the care of a patient at home, oral administration of the antibacterial agent is more convenient and the clinical usability is extremely high. It has been strongly desired in the clinical field to develop a carbapenem compound which has a potent antibacterial activity especially against *Haemophilus influenzae* (which widely gains resistance to the inhibitory effect of existing β-lactam agents together with mutation of penicillin binding proteins, such as β-lactamase, non-producing ampicillin resistant *Haemophilus influenzae*, and penicillin resistant *Streptococcus pneumonia*. All of them have a structural property having 1 β-methyl group and a side chain via sulfide bond which are said to contribute to an increase of chemical stability and biological stability, and are modified to a prodrug for increase of oral absorbability.

On the other hand, carbapenem compounds having an aryl ring via C—C bond as a side chain structure were known since 1980s (see e.g., U.S. Pat. Nos. 4,543,257, 4,775,669, and 5,258,509, Tetrahedron, 1983, Vol. 39, p 2531-2549, and Journal of Medicinal Chemistry, 1987, Vol. 30, p 871-880). However, these reports are concerned only to studies and developments on injections.

Although International Publication Nos. WO 02/053566, WO 03/040146 and WO 03/089431 relate to agents for oral administration, the substituent at position 3 of 7-oxo-1-azabicyclo[3.2.0]hept-2-ene which is a basic nucleus of the carbapenem compound is limited to a monocyclic ring such as benzene, thiophene or pyridine ring. As the substituent at position 3, carbapenem compounds having only naphthalene ring (as bicyclic ring wherein benzene ring fused with another cyclic ring) are known (U.S. Pat. Nos. 5,006,519 and 5,032,587, European Patent Nos. EP 466253B and EP 466254B), but other substituents on said position 3 are not referred to therein and such compounds are not applied for oral administration.

Therefore, carbapenem derivatives having substituents at various locations are known; however, carbapenem derivatives having substituents at the 5 and/or 6 position of the carbapenem core compound have not been reported.

SUMMARY OF THE INVENTION

The present invention provides a carbapenem compound having the formula

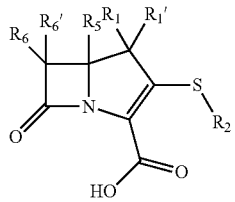

wherein R1 and R1' are selected from the group, —H, —CH$_3$, —CH$_2$OH, —CH$_2$OCONHR*, —CONHR*, —CO$_2$H, —CH$_2$OH, —CH$_2$OCONHR*, —CONHR*, —CO$_2$H, —CH$_2$OH, —CH$_2$OCONHR*, —CONHR*, —CO$_2$H, —CHOHCH$_3$, —CH$_2$OCONHR*, —CONHR*, and —CO$_2$H; R2 is selected from —H, —(CH$_2$)$_2$NHCHNH, and -(cy-C$_4$H$_7$N)CONMe$_2$; R5 is selected from —H, —CH$_3$, —CH$_2$NR*, —CH$_2$OCONR*, and —CH$_2$COCONHR*; R6 and R6' are selected from —H, and —CHOHCH$_3$; and R* are independently a hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. For example, the compositions may be an C1α-C1β di-substituted carbapenem compound, an C5α substituted carbapenem compound, an C6α-C6β di-substituted carbapenem compound.

For example R2 may be a {2-[(iminomethyl)amino]ethyl}; [5-(dimethylcarbamoyl)pyrrolidin-2-yl]; [(3S,5S)-5-[(3-carboxyphenyl)carbamoyl]pyrrolidin-3-yl]; [(3S,5S)-5-[(sulfamoylamino)methyl]pyrrolidin-3-yl]; {[(3S)-1-ethanimidoylpyrrolidin-3-yl]; or (6,7-dihydro-5H-pyrazolo[1,2-a][1,2,4]triazol-8-ium-6-ylsulfanyl). R2 may be a —(CH$_2$)$_2$NHCHNH, or -(cy-C$_4$H$_7$N)CONMe$_2$. The present disclosure provides a C5α substituted carbapenem compound, C1α-C1β di-substituted carbapenem compound and a C6α-C6β di-substituted carbapenem compound.

The disclosure provides a composition wherein R5 may be a —H, R6 may be a —H, R6' may be a —CHOHCH$_3$ and R1 is a —CH$_2$OH, R1' is a —CH$_3$, R2 is a —(CH$_2$)$_2$NHCHNH; R1 is a —CH$_2$OCONHR3*, R1' is a —CH$_3$, R2 is a —(CH$_2$)$_2$NHCHNH; R1 is a —CONHR3*, R1' is a —CH$_3$, R2 is a —(CH$_2$)$_2$NHCHNH; R1 is a —CO$_2$H, R1' is a —CH$_3$, R2 is a —(CH$_2$)$_2$NHCHNH; R1 is a —CH$_2$OH, R1' is a —CH$_3$, R2 is a -(cy-C$_4$H$_7$N)CONMe$_2$; R1 is a —CH$_2$OCONHR3*, R1' is a —CH$_3$, R2 is a -(cy-C$_4$H$_7$N)CONMe$_2$; R1 is a —CONHR3*, R1' is a —CH$_3$, R2 is a -(cy-C$_4$H$_7$N)CONMe$_2$; R1 is a —CO$_2$H, R1' is a —CH$_3$, R2 is a -(cy-C$_4$H$_7$N)CONMe$_2$; R1 is a —CH$_2$OH, R1' is a —H, R2 is a —(CH$_2$)$_2$NHCHNH; R1 is a —CH$_2$OCONHR3*, R1' is a —H, R2 is a —(CH$_2$)$_2$NHCHNH; R1 is a —CONHR3*, R1' is a —H, R2 is a —(CH$_2$)$_2$NHCHNH; R1 is a —CO$_2$H, R1' is a —H, R2 is a —(CH$_2$)$_2$NHCHNH; R1 is a —CH$_2$OH, R1' is a —H, R2 is a -(cy-C$_4$H$_7$N)CONMe$_2$; R1 is a —CH$_2$OCONHR3*, R1' is a —H, R2 is a -(cy-C$_4$H$_7$N)CONMe$_2$; R1 is a —CONHR3*, R1' is a —H, R2 is a -(cy-C$_4$H$_7$N)CONMe$_2$; R1 is a —CO$_2$H, R1' is a —H, R2 is a -(cy-C$_4$H$_7$N)CONMe$_2$; R1 is a —CH$_2$OH, R1' is a —CH$_3$, R2 is a —(CH$_2$)$_2$NHCHNH; R1 is a —CH$_2$OCONHR3*, R1' is a —CH$_3$, R2 is a —(CH$_2$)$_2$NHCHNH; R1 is a —CONHR3*, R1' is a —CH3, R2 is a —(CH2)2NHCHNH; R1 is a —CO$_2$H, R1' is a —CH$_3$, R2 is a —(CH$_2$)$_2$NHCHNH; R1 is a —CH$_2$OH, R1' is a —CH$_3$, R2 is a -(cy-C$_4$H$_7$N)CONMe$_2$; R1 is a —CH$_2$OCONHR3*, R1' is a —CH$_3$, R2 is a -(cy-C$_4$H$_7$N)CONMe$_2$; R1 is a —CONHR3*, R1' is a —CH$_3$, -(cy-C$_4$H$_7$N)CONMe$_2$; R1 is a —CO$_2$H, R1' is a —CH$_3$, R2 is a -(cy-C$_4$H$_7$N)CONMe$_2$; or R1 is a —CH$_2$OH, R1' is a —H, R2 is a —(CH$_2$)$_2$NHCHNH.

The present invention provides a antibacterial agent containing the carbapenem compound or its pharmaceutically acceptable salt having the formula as an active ingredient

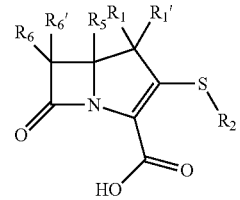

wherein R1 and R1' are selected from the group, —H, —CH$_3$, —CH$_2$OH, —CH$_2$OCONHR*, —CONHR*, —CO$_2$H, —CH$_2$OH, —CH$_2$OCONHR*, —CONHR*, —CO$_2$H, —CH$_2$OH, —CH$_2$OCONHR*, —CONHR*, —CO$_2$H, —CHOHCH$_3$, —CH$_2$OCONHR*, —CONHR*, and —CO$_2$H; R2 is selected from —H, —(CH$_2$)$_2$NHCHNH, and -(cy-C$_4$H$_7$N)CONMe$_2$; R5 is selected from —H, —CH$_3$, —CH$_2$NR*, —CH$_2$OCONR*, and —CH$_2$COCONHR*; R6 and R6' are selected from —H, and —CHOHCH$_3$, R* are independently a hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl; and a pharmaceutically acceptable carrier, excipient, binder or stabilizer.

The disclosure provides an antibacterial agent containing the carbapenem compound or its pharmaceutically acceptable salt. R2 may be a {2-[(iminomethyl)amino]ethyl}; [5-(dimethylcarbamoyl) pyrrolidin-2-yl]; [(3S,5S)-5-[(3-carboxyphenyl)carbamoyl]pyrrolidin-3-yl]; [(3S,5S)-5-[(sulfamoylamino)methyl]pyrrolidin-3-yl]; {[(3S)-1-ethanimidoylpyrrolidin-3-yl]; or (6,7-dihydro-5H-pyrazolo[1,2-a][1,2,4]triazol-8-ium-6-ylsulfanyl). R2 may be a —(CH$_2$)$_2$NHCHNH, or -(cy-C$_4$H$_7$N)CONMe$_2$. The disclosure provides a composition wherein R5 may be a —H, R6 may be a —H, R6' may be a —CHOHCH$_3$ and R1 is a —CH$_2$OH, R1' is a —CH$_3$, R2 is a —(CH$_2$)$_2$NHCHNH; R1 is a —CH$_2$OCONHR3*, R1' is a —CH$_3$, R2 is a —(CH$_2$)$_2$NHCHNH; R1 is a —CONHR3*, R1' is a —CH$_3$, R2 is a —(CH$_2$)$_2$NHCHNH; R1 is a —CO$_2$H, R1' is a —CH$_3$, R2 is a —(CH$_2$)$_2$NHCHNH; R1 is a —CH$_2$OH, R1' is a —CH$_3$, R2 is a -(cy-C$_4$H$_7$N)CONMe$_2$; R1 is a —CH$_2$OCONHR3*, R1' is a —CH$_3$, R2 is a -(cy-C$_4$H$_7$N)CONMe$_2$; R1 is a —CONHR3*, R1' is a —CH$_3$, R2 is a -(cy-C$_4$H$_7$N)CONMe$_2$; R1 is a —CO$_2$H, R1' is a —CH$_3$, R2 is a -(cy-C$_4$H$_7$N)CONMe$_2$; R1 is a —CH$_2$OH, R1' is a —H, R2 is a —(CH$_2$)$_2$NHCHNH; R1 is a —CH$_2$OCONHR3*, R1' is a —H, R2 is a —(CH$_2$)$_2$NHCHNH; R1 is a —CONHR3*, R1' is a —H, R2 is a —(CH$_2$)$_2$NHCHNH; R1 is a —CO$_2$H, R1' is a —H, R2 is a —(CH$_2$)$_2$NHCHNH; R1 is a —CH$_2$OH, R1' is a —H, R2 is a -(cy-C$_4$H$_7$N)CONMe$_2$; R1 is a —CH$_2$OCONHR3*, R1' is a —H, R2 is a -(cy-C$_4$H$_7$N)CONMe$_2$; R1 is a —CONHR3*, R1' is a —H, R2 is a -(cy-C$_4$H$_7$N)CONMe$_2$; R1 is a —CO$_2$H, R1' is a —H, R2 is a -(cy-C$_4$H$_7$N)CONMe$_2$; R1 is a —CH$_2$OH, R1' is a —CH$_3$, R2 is a —(CH$_2$)$_2$NHCHNH; R1 is a —CH$_2$OCONHR3*, R1' is a —CH$_3$, R2 is a —(CH$_2$)$_2$NHCHNH; R1 is a —CONHR3*, R1' is a —CH3, R2 is a —(CH2)2NHCHNH; R1 is a —CO$_2$H, R1' is a —CH$_3$, R2 is a —(CH$_2$)$_2$NHCHNH; R1 is a —CH$_2$OH, R1' is a —CH$_3$, R2 is a -(cy-C$_4$H$_7$N)CONMe$_2$; R1 is a —CH$_2$OCONHR3*, R1' is a —CH$_3$, R2 is a -(cy-C$_4$H$_7$N)CONMe$_2$; R1 is a —CONHR3*, R1' is a —CH$_3$, -(cy-C$_4$H$_7$N)CONMe$_2$; R1 is a —CO$_2$H, R1' is a —CH$_3$, R2 is a -(cy-C$_4$H$_7$N)CONMe$_2$; or R1 is a —CH$_2$OH, R1' is a —H, R2 is a —(CH$_2$)$_2$NHCHNH.

The present invention provides a carbapenem compound process for preparing a compound below:

wherein R1 and R1' are selected from the group, —H, —CH$_3$, —CH$_2$OH, —CH$_2$OCONHR*, —CONHR*, —CO$_2$H, —CH$_2$OH, —CH$_2$OCONHR*, —CONHR*, —CO$_2$H, —CH$_2$OH, —CH$_2$OCONHR*, —CONHR*, —CO$_2$H, —CHOHCH$_3$, —CH$_2$OCONHR*, —CONHR*, and —CO$_2$H; R2 is selected from —H, —(CH$_2$)$_2$NHCHNH, and -(cy-C$_4$H$_7$N)CONMe$_2$; R5 is selected from —H, —CH$_3$, —CH$_2$OR*, —CH$_2$OCONR*, and —CH$_2$COCONHR*; R6 and R6' are selected from —H, and —CHOHCH$_3$, R* are independently a hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl.

R2 may be a {2-[(iminomethyl)amino]ethyl}; [5-(dimethylcarbamoyl)pyrrolidin-2-yl]; [(3S,5S)-5-[(3-carboxyphenyl)carbamoyl]pyrrolidin-3-yl]; [(3S,5S)-5-[(sulfamoylamino)methyl]pyrrolidin-3-yl]; {[(3S)-1-ethanimidoylpyrrolidin-3-yl]; or (6,7-dihydro-5H-pyrazolo[1,2-a][1,2,4]triazol-8-ium-6-ylsulfanyl). R2 may be a —(CH$_2$)$_2$NHCHNH, or -(cy-C$_4$H$_7$N)CONMe$_2$. R2 may be a {2-[(iminomethyl)amino]ethyl}; [5-(dimethylcarbamoyl) pyrrolidin-2-yl]; [(3S,5S)-5-[(3-carboxyphenyl)carbamoyl]pyrrolidin-3-yl]; [(3S,5S)-5-[(sulfamoylamino)methyl]pyrrolidin-3-yl]; {[(3S)-1-ethanimidoylpyrrolidin-3-yl]; or (6,7-dihydro-5H-pyrazolo[1,2-a][1,2,4]triazol-8-ium-6-ylsulfanyl). R2 may be a —(CH$_2$)$_2$NHCHNH, or -(cy-C$_4$H$_7$N)CONMe$_2$. The disclosure provides a composition wherein R5 may be a —H, R6 may be a —H, R6' may be a —CHOHCH$_3$ and R1 is a —CH$_2$OH, R1' is a —CH$_3$, R2 is a —(CH$_2$)$_2$NHCHNH; R1 is a —CH$_2$OCONHR3*, R1' is a —CH$_3$, R2 is a —(CH$_2$)$_2$NHCHNH; R1 is a —CONHR3*, R1' is a —CH$_3$, R2 is a —(CH$_2$)$_2$NHCHNH; R1 is a —CO$_2$H, R1' is a —CH$_3$, R2 is a —(CH$_2$)$_2$NHCHNH; R1 is a —CH$_2$OH, R1' is a —CH$_3$, R2 is a -(cy-C$_4$H$_7$N)CONMe$_2$; R1 is a —CH$_2$OCONHR3*, R1' is a —CH$_3$, R2 is a -(cy-C$_4$H$_7$N)CONMe$_2$; R1 is a —CONHR3*, R1' is a —CH$_3$, R2 is a -(cy-C$_4$H$_7$N)CONMe$_2$; R1 is a —CO$_2$H, R1' is a —CH$_3$, R2 is a -(cy-C$_4$H$_7$N)CONMe$_2$; R1 is a —CH$_2$OH, R1' is a —H, R2 is a —(CH$_2$)$_2$NHCHNH; R1 is a —CH$_2$OCONHR3*, R1' is a —H, R2 is a —(CH$_2$)$_2$NHCHNH; R1 is a —CONHR3*, R1' is a —H, R2 is a —(CH$_2$)$_2$NHCHNH; R1 is a —CO$_2$H, R1' is a —H, R2 is a —(CH$_2$)$_2$NHCHNH; R1 is a —CH$_2$OH, R1' is a —H, R2 is a -(cy-C$_4$H$_7$N)CONMe$_2$; R1 is a —CH$_2$OCONHR3*, R1' is a —H, R2 is a -(cy-C$_4$H$_7$N)CONMe$_2$; R1 is a —CONHR3*, R1' is a —H, R2 is a -(cy-C$_4$H$_7$N)CONMe$_2$; R1 is a —CO$_2$H, R1' is a —H, R2 is a -(cy-C$_4$H$_7$N)CONMe$_2$; R1 is a —CH$_2$OH, R1' is a —CH$_3$, R2 is a —(CH$_2$)$_2$NHCHNH; R1 is a —CH$_2$OCONHR3*, R1' is a —CH$_3$, R2 is a —(CH$_2$)$_2$NHCHNH; R1 is a —CONHR3*, R1' is a —CH3, R2 is a —(CH2)2NHCHNH; R1 is a —CO$_2$H, R1' is a —CH$_3$, R2 is a —(CH$_2$)$_2$NHCHNH; R1 is a —CH$_2$OH, R1' is a —CH$_3$, R2 is a -(cy-C$_4$H$_7$N)CONMe$_2$; R1 is a —CH$_2$OCONHR3*, R1' is a —CH$_3$, R2 is a -(cy-C$_4$H$_7$N)CONMe$_2$; R1 is a —CONHR3*, R1' is a —CH$_3$, -(cy-C$_4$H$_7$N)CONMe$_2$; R1 is a —CO$_2$H, R1' is a —CH$_3$, R2 is a -(cy-C$_4$H$_7$N)CONMe$_2$; or R1 is a —CH$_2$OH, R1' is a —H, R2 is a —(CH$_2$)$_2$NHCHNH.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
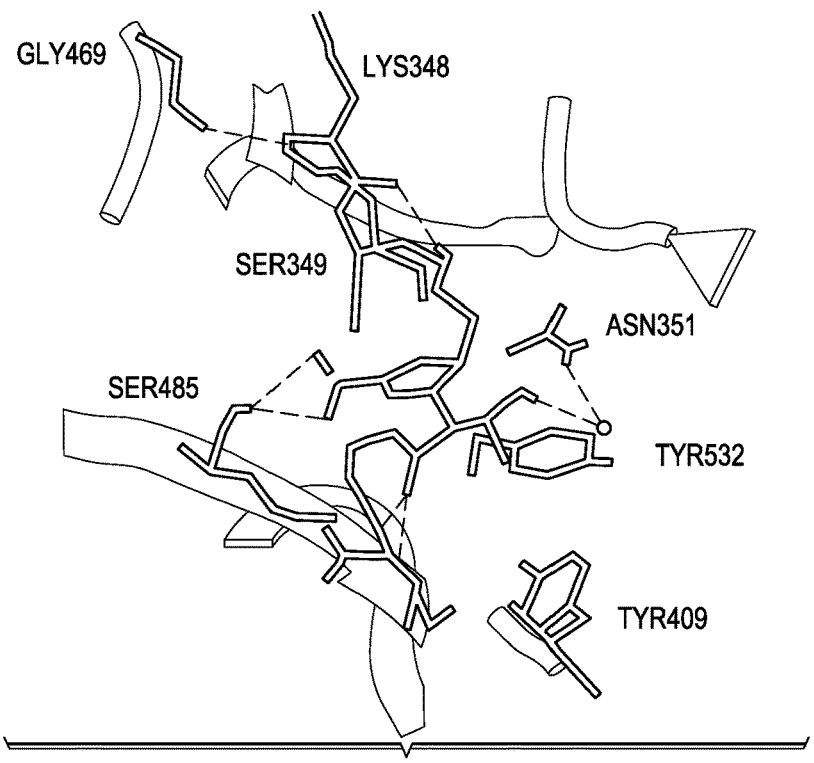
FIG. 1a is an image of the complex of imipenem with PBP3 of P. aeruginosa (3PBQ)

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention recognized that the potent and broad-spectrum bactericidal activity and relatively low toxicity, the β-lactam class of antibiotics continues to be a clinical mainstay and the β-lactams currently make-up about half the commercial antibacterial market. Increased use of β-lactams has predictably resulted in emergence of resistance which takes the form of β-lactamase production, target modifications, and, in the case of Gram negative pathogens, outer membrane permeability modifications and up-regulated efflux. Carbapenems represent the most potent and reliable of the β-lactams and are usually reserved as the antibiotics of last resort. Unfortunately, carbapenem resistance is dramatically increasing, due primarily to the acquisition of genes coding for one or more carbapenemases. Carbapenamases may be either serine- (classes A, C, and D) or metallo- (class B) β-lactamases, together with porin deletions and up-regulated efflux. Numerous mechanistic studies of the slowed hydrolysis rate of carbapenems by classes A, C, and D β-lactamases have been reported. β-Lactamase stability is attributed to a rate of deacylation of the resultant (AE), primarily due to interactions of the 6α-((1'R)-hydroxyethyl) group with the hydrolytic water molecule which displaces it and changes its hydrogen-bonding network. A conformational change of the AE has also been observed as has movement of the carbonyl oxygen of the AE out of the oxyanion hole in some cases.

SAR of the carbapenem scaffold was thus optimized with emphasis on obtaining maximal inherent antibacterial activity. All commercial carbapenems produced in the past twenty years have maintained this original carbapenem scaffold, while incorporating new structural moieties at C2 (in addition to a C1α-methyl group to improve stability to renal dehydropeptidase). The present invention provides structural modifications of the carbapenem scaffold at positions other than C2 to confer improved stability to carbapenemases, either serine- or metallo-. The present invention provides structural modifications of the carbapenem scaffold to increase the β-lactamase stability conferred by these structural modifications to produce an antibiotic with broad spectrum activity against carbapenemase-producing strains. Since, carbapenems have inherent potencies far superior to other types of β-lactam antibiotic, the modified carbapenems of the present invention even with reduced activity would be tolerated if it resulted in significant increases in carbapenemase stability.

In addition, the present invention provides carbapenems structures with enhanced penicillin-binding protein (PBP) transpeptidase-carbapenem acyl-enzymes (AEs) affinity and thus enhanced antibacterial activity. The present invention also provides carbapenems structures with enhanced antibacterial potency; enhanced stability to serine carbapenemases (classes A and D); and enhanced stability to metallo carbapenemases.

The present invention provides structural modifications of the carbapenem scaffolds that render these antibiotics more stable to hydrolytic enzymes. As the clinical frequency of antibacterial resistance continues to escalate, increasing use is being made of carbapenems, which represent the most potent and reliable class of β-lactam antibiotic. The present invention provides mono- and di-substituted carbapenems that include C1-disubstituted carbapenems, C5 substituted carbapenems, and C6-disubstituted carbapenems. The biological activity of novel carbapenems is evaluated by the microbiological profiling vs carbapenem-susceptible and resistant organisms, in vitro assay for PBP inhibition, in vitro assays for hydrolysis by and inhibition of serine- and metallo-carbapenemases, in vitro assay for susceptibility to human renal dipeptidase-1, in vitro drug metabolism and pharmacokinetic (DMPK) assays.

The present invention provides modifications that increase steric bulk to slow initial acylation of both the active site serine of the PBPs as well as the serine β-lactamases (SBLs). It is noted that the inherent chemical acylating ability of carbapenems can also be augmented by suitable electronegative substituents at C2 and that the recognition of the antibiotic by the metallo-β-lactamases (MBLs) is quite different from that of the PBPs and/or SBLs. More importantly, however, the added bulk slows deacylation of the resultant respective AEs, leading to more efficient antibiotics and also improving inhibition of serine β-lactamases. Some of the modifications include C5α substitutions, e.g., methyl group.

Figure 1B:
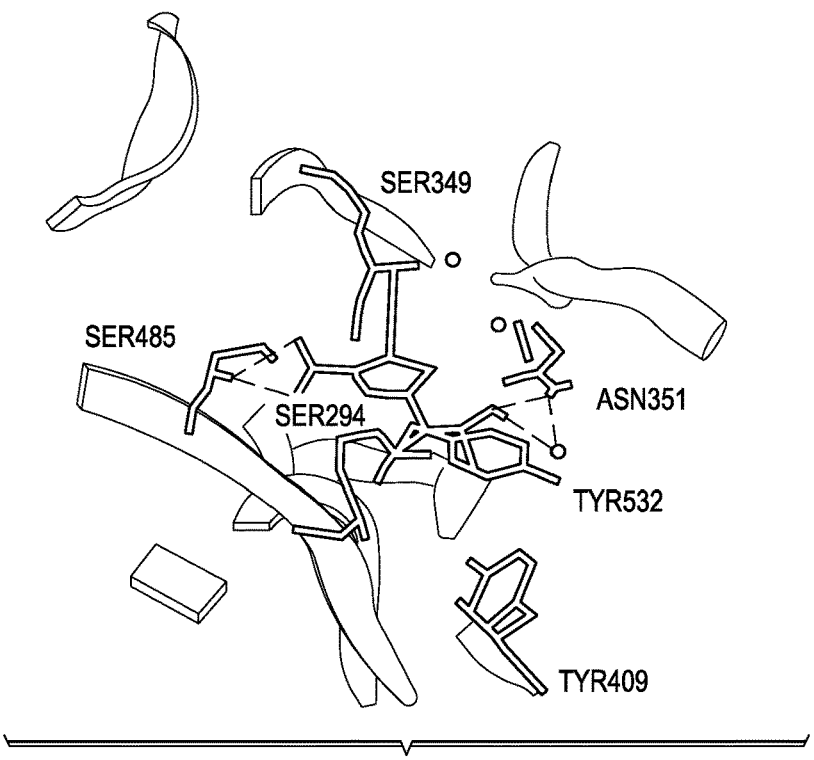
FIG. 1b is an image of a computationally modified imipenem complex illustrating the predicted interaction of proposed 1α-(hydroxyethyl) imipenem side chain with carbonyl of LYS348 and SER349.
Figure 1C:
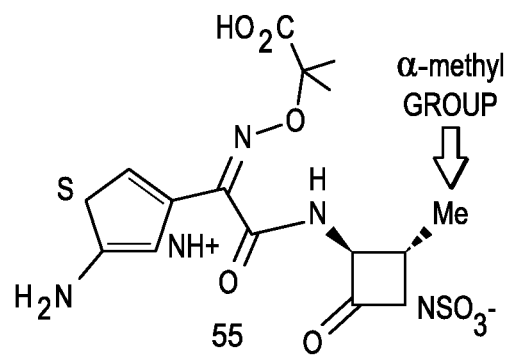
FIG. 1c is an image of the structures of aztreonam.
Figure 1D:
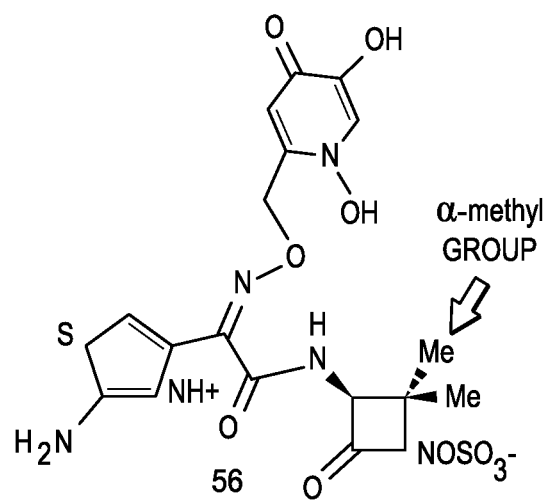
FIG. 1d is an image of the structures of BAL30072.

FIG. 1a is an image of the complex of imipenem with PBP3 of P. aeruginosa (3PBQ). FIG. 1b is an image of a computationally modified imipenem complex illustrating the predicted interaction of proposed 1α-(hydroxyethyl) imipenem side chain with carbonyl of LYS348 and SER349. FIG. 1c is an image of the structures of aztreonam; and FIG. 1d is an image of the structures of BAL30072. Structures of carbapenem-β-lactamase AEs and recently, covalent carbapenem-PBP complexes have been reported and enabled computational evaluations. The present invention provides a carbapenem with enhanced PBP3 (lethal target of aztreonam) affinity. Such modification, involving incorporation of a C1α-hydroxyethyl substituent into the carbapenem, is shown in FIG. 1b which was generated by manual modification of PDB file 3PBQ, a covalent complex of PBP3 and imipenem. The hydroxyethyl group is predicted to be capable of hydrogen bonding to the backbone carbonyl of LYS348 (and the carbonyl of SER349). While it is difficult to assess the binding of this modified carbapenem to PBP2 (carbapenem lethal target), since no P. aeruginosa PBP2 structural data is available, the generation of a carbapenem with an alternate target would be useful.

The present invention provides numerous approaches to the generation of a carbapenem either resistant to hydrolysis or one which functions as a carbapenemase inhibitor with respect to serine β-lactamases. For example, the present invention provides the introduction of structural alterations which disfavor complexation of the antibiotic (i.e. raise the Km). This suffers from a limitation that the modified antibiotic must also be recognized by the related transpeptidases (TPs). The present invention provides the introduction of structural alterations which prolong the lifetime of the AE. This could occur due to increased chemical hydrolytic stability, increased steric hindrance near the carbonyl carbon of the AE, displacement of hydrolytic water, movement of the carbonyl oxygen of the AE out of the oxyanion hole, and/or inhibitor-induced conformational changes in the enzyme. The present invention provides the introduction of structural alterations which disfavor the decomplexation of the hydrolyzed antibiotic. Since some variables, such as conformational changes of the enzyme in the AE complex, are impossible to predict computationally, it is necessary to evaluate focused libraries of substituents at each position in a systematic combinatorial manner. Selected structural features of carbapenems, such as the C6α ((1'R)-hydroxyethyl) substituent, are known to be required for activity and will remain constant.

Figure 2:
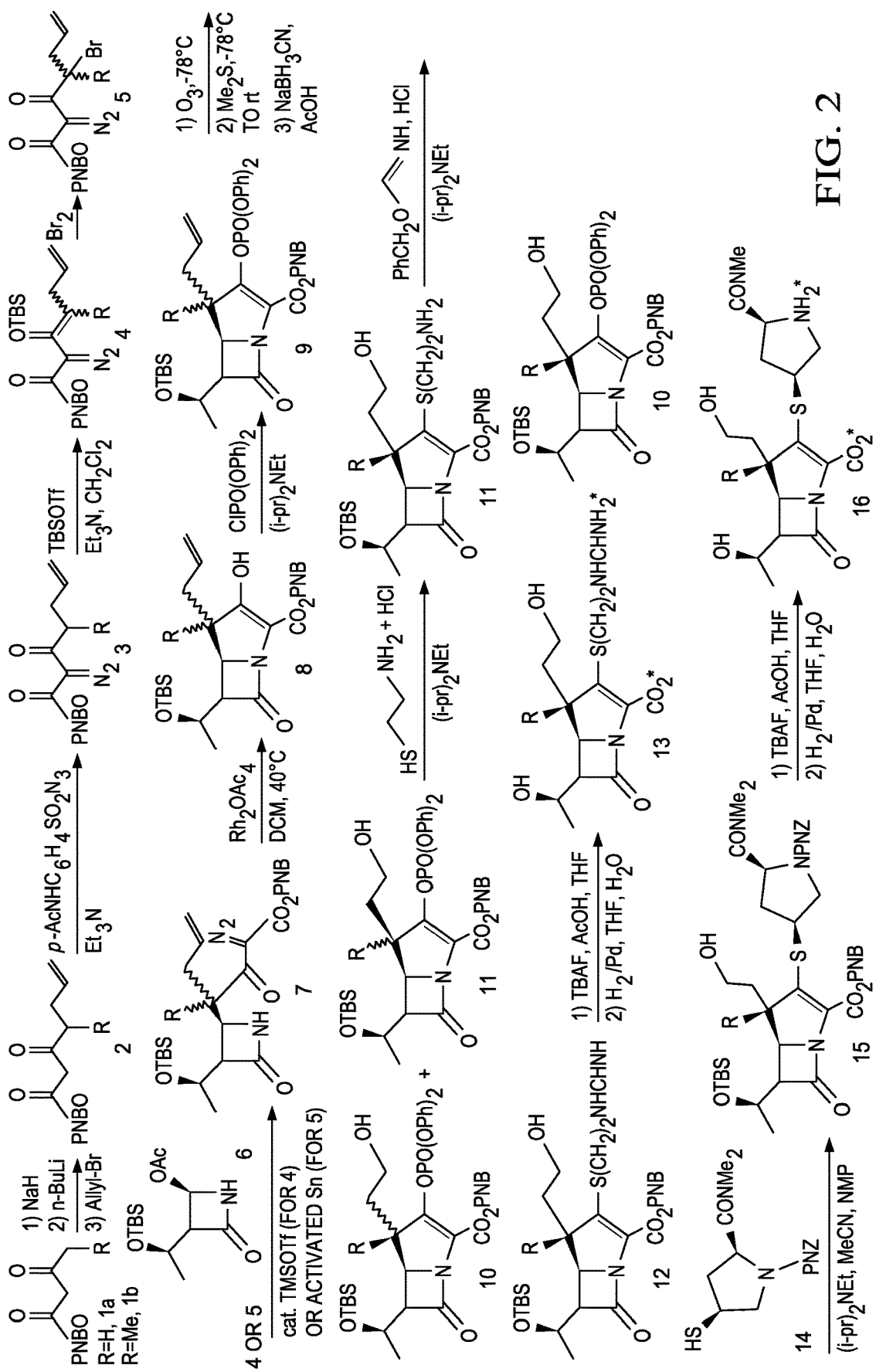
FIG. 2 is and image of the synthesis of C1-hydroxyethyl- and C1-methyl-C1-(hydroxyethyl)carbapenems.
Figure 3:
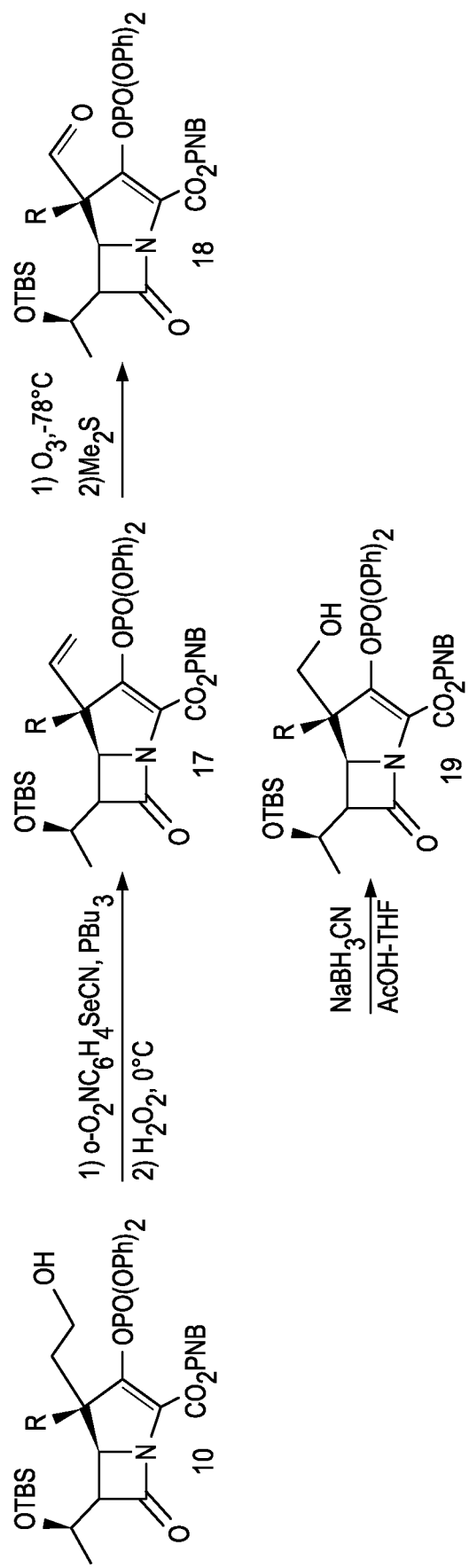
FIG. 3 is an image of the synthesis of C1-hydroxymethyl- and C1-methyl-C1-(hydroxymethyl)carbapenems.
Figure 4:
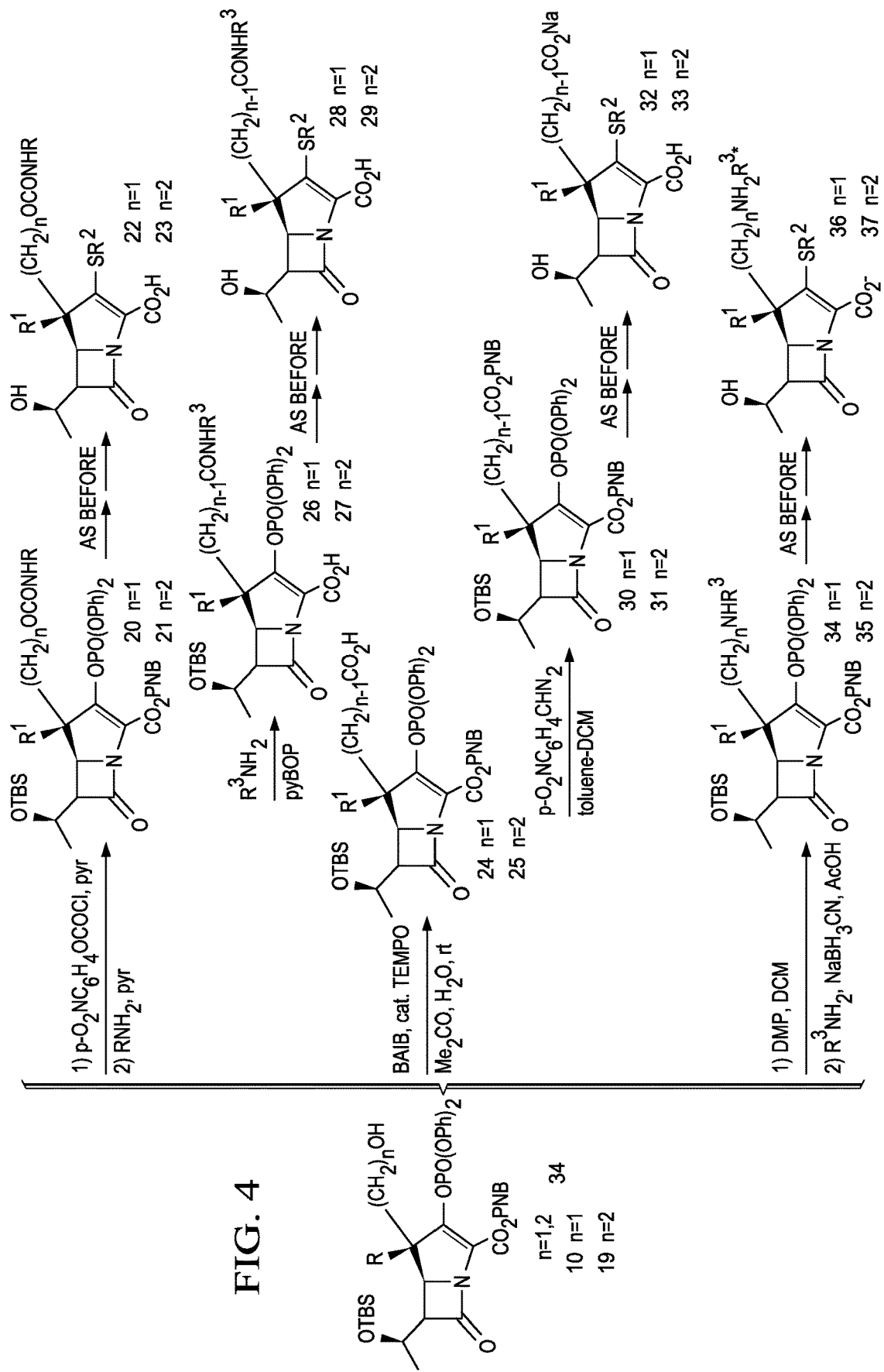
FIG. 4 is an image of the synthesis of C1-substituted carbapenems, including carbamates, amides, and acids.
Figure 5:
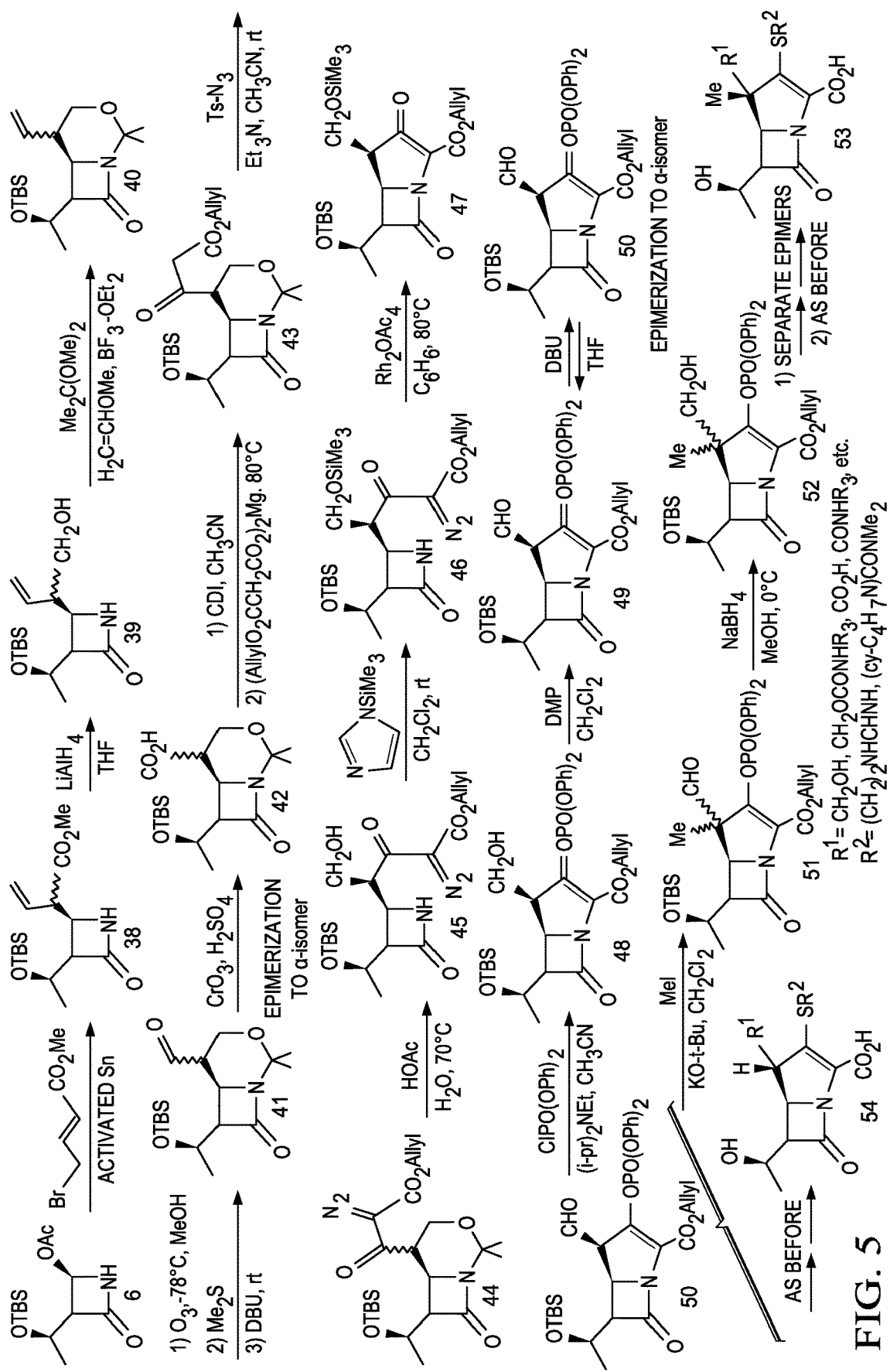
FIG. 5 is an image of the Alternative synthesis of C1-substituted carbapenems.

Carbapenems of the present invention are highly functional molecules, often displaying chemical instability. Library design is strongly affected not only by what would be structurally desirable but by synthetic and stability considerations. The present invention provides reliable synthetic entries to the target scaffold and provides alternate synthetic strategies. The present invention provides schemes targeted toward incorporation of structural features at atypical positions, including C1α, C5β, and C6α, expected to affect interaction with the target enzymes and/or influence the stability of the AEs. For example, the present invention provides synthesis of C1α-monosubstituted and C1-disubstituted-carbapenems, including the synthesis and characterization a typically C1 substituted carbapenems C1α-methyl, C1α-hydroxymethyl, C1α-hydroxyethyl carbapenems with positively charged C2 side chains. The C1α-methyl group, is known to impart chemical stability and stability to renal DHP. FIGS. 2-5 illustrate entries to 1α-substituted carbapenems and 1,1-disubstituted carbapenems. Utilization is made of the highly functional silyl enol ether of diazoketoester 4 or the corresponding bromoketoester 5, which enable introduction of pyrrolidine functionality in one step. The reaction can succeed with a tetrasubstituted enol ether. Commercial azetidinone 6 enables access to C5 and C6 stereochemistry. Regarding the nature of C1α-substituents, substituents larger than methyl have been incorporated at C1β but little is reported at C1α. Modeling indicates the α-face has opportunity to interact with all classes of β-lactamase and TPs (w.r.t. PBP3 carbapenem AE, there is space to accommodate up to four or five atoms at C1α). FIG. 2 is an image of the synthesis of C1α-hydroxyethyl- and C1β-methyl-C1α-(hydroxyethyl)carbapenems. FIG. 3 is an image of the synthesis of C1α-hydroxymethyl- and C1β-methyl-C1α-(hydroxymethyl)carbapenems. FIG. 4 is an image of the synthesis of C1α-substituted carbapenems, including carbamates, amides, and acids. Removing a carbon to generate the hydroxymethyl analog is feasible, providing two alcohols from which to make analogs, including carbamates, carboxylic acid derivatives, and amines FIG. 5 is an image of the alternative synthesis of C1-substituted carbapenems.

Figures 6, 7:
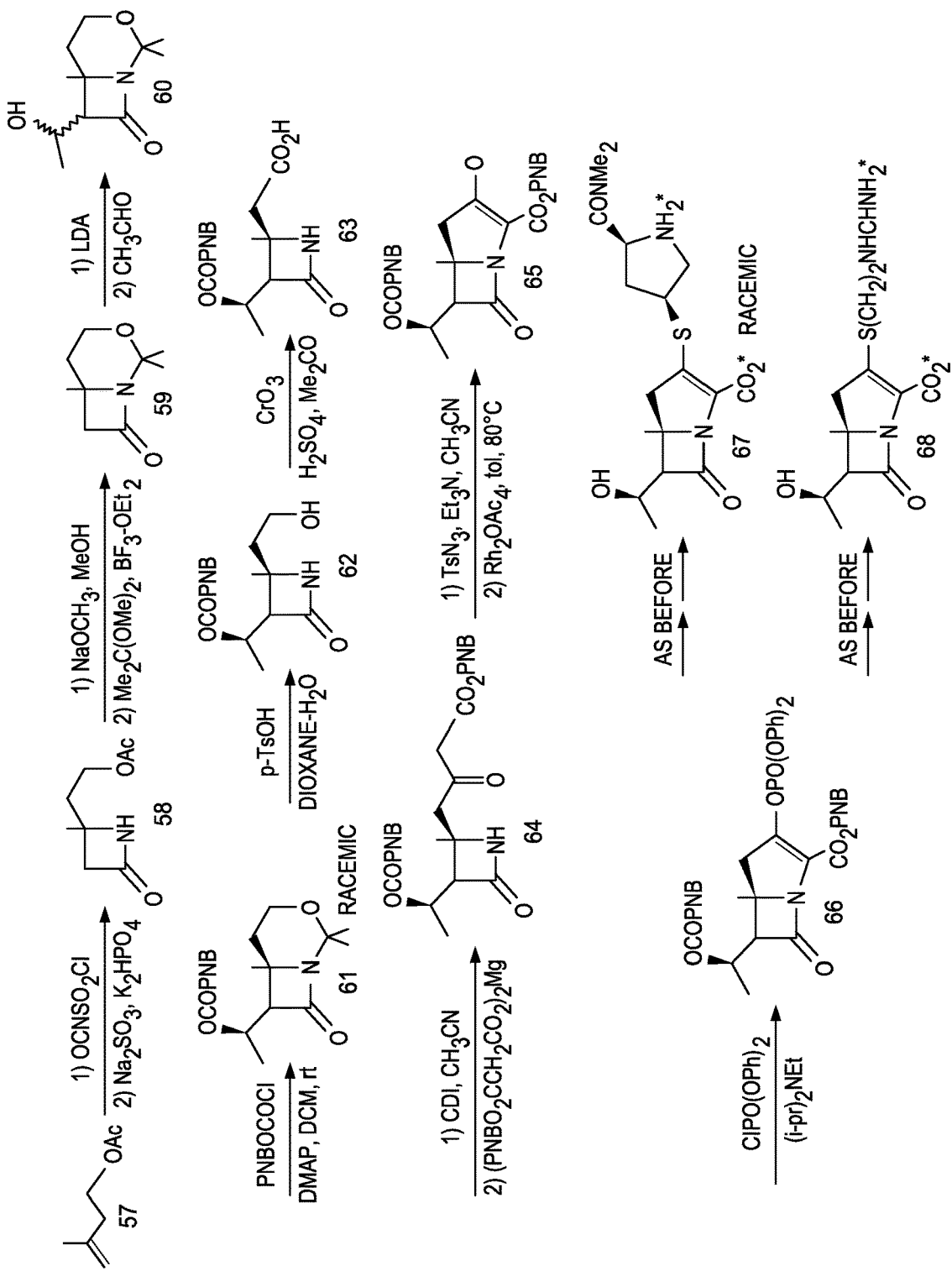
FIG. 6 is an image of the synthesis of racemic C5α-methylcarbapenems. Synthesis of C5α-(substituted) carbapenems.

FIG. 6 is an image of the synthesis of racemic C5α-methylcarbapenems. Synthesis of C5α-(substituted) carbapenems. Synthesis and characterization of C5α-substituted carbapenems, including C5α-methyl, and C5α-(hydroxymethyl)carbapenems. Aztreonam (FIG. 1c) is the only commercial β-lactam with a non-hydrogen substituent at a location analogous to carbapenem C5α and the only current commercial β-lactam with general MBL stability. Sulfactam 56 also possesses MBL stability. This stability may be due to the a typical substitution pattern (i.e. at C4α of the monocyclic azetidin-2-one). Possibly due to the synthetic challenges in preparing analogous C5α-substituted analogs of bicyclic β-lactams, the SAR of C5α substituted bicyclics (carbapenems, penams, penems, and clavams and corresponding C6α-position of cephems) is virtually unexplored in the current art. The present invention provides a C5αmethyl- or hydroxymethyl-group substitutions that impart MBL and/or additional SBL stability (without affecting, or improving, TP affinity) would have significance. A synthesis of racemic C5α methyl carbapenems is detailed in FIG. 6.

Figure 7A:
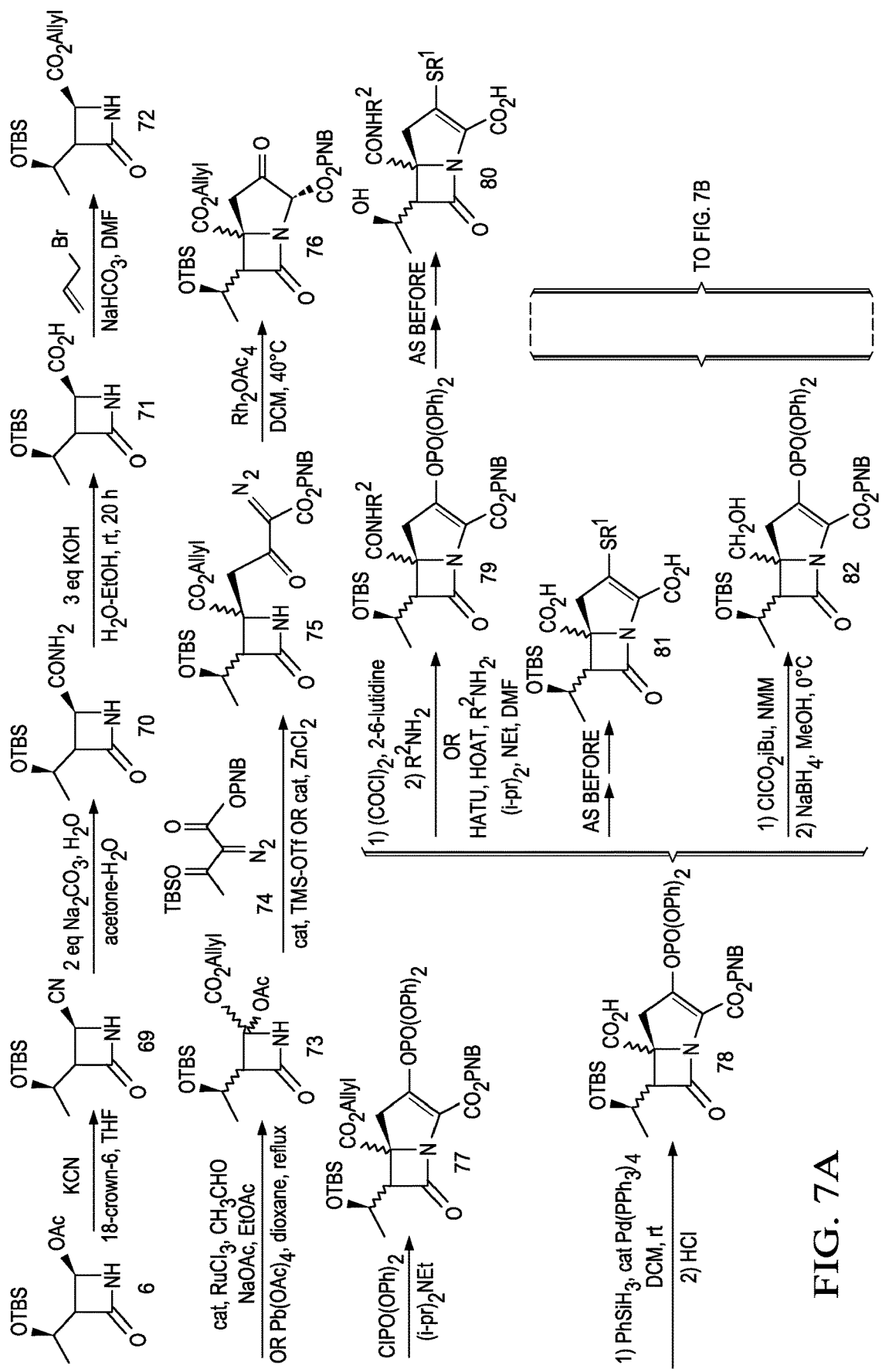
FIGS. 7A and 7B is an image of the stereospecific synthesis of C5-substituted carbapenems. The synthesis makes use of chiral azetidinone 6, which is further functionalized at C4 by oxidation of the azetidinone.
Figure 7B:
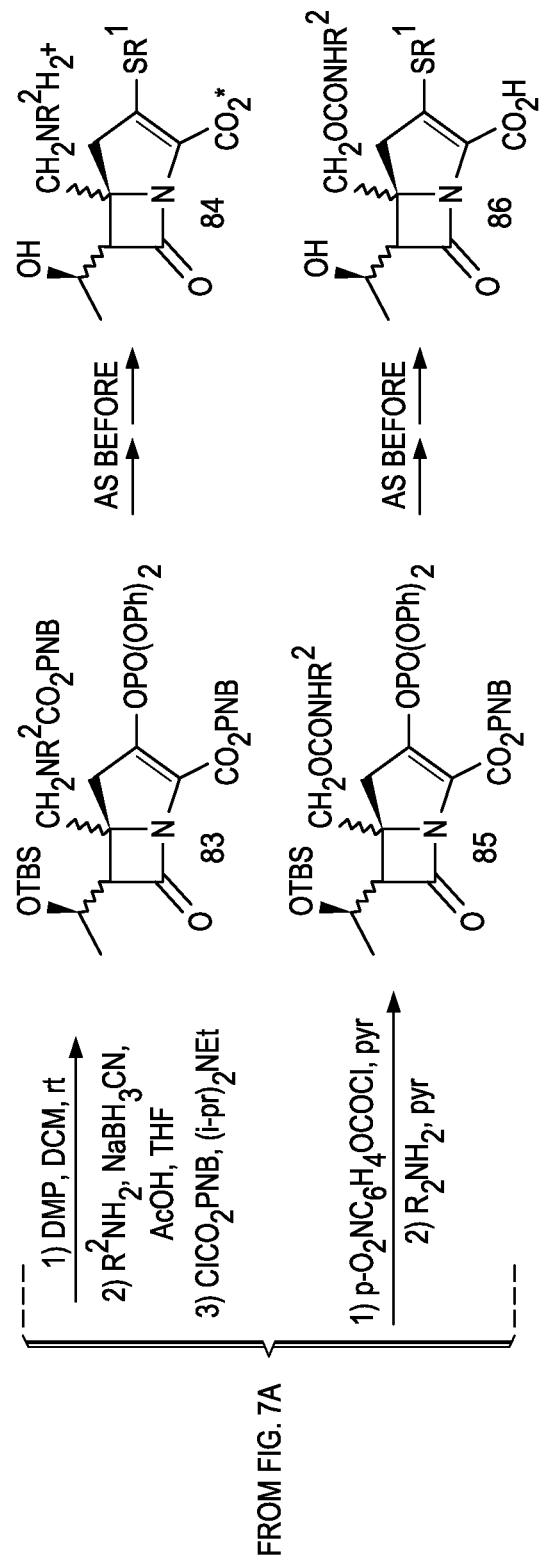

FIGS. 7A and 7B is an image of the stereospecific synthesis of C5-substituted carbapenems. The synthesis makes use of chiral azetidinone 6, which is further functionalized at C4 by oxidation of the azetidinone.

Synthesis of C6-(disubstituted)carbapenems. Synthesis and characterization of C6-disubstituted carbapenems, each having a C6α-(1R)-hydroxyethyl side chain and positively charged C2 side chains. C6-Disubstituted carbapenems possessing the prerequisite 6α-((1'R)-hydroxyethyl) group are virtually unknown. Provided such carbapenems can acylate the active site serines in both the TPs and in the serine β-lactamases, the added steric bulk provided by incorporation of a α-face alkyl (or hydroxyalkyl) group should hinder deacylation and could promote rotation of the carbonyl oxygen of the AE out of the oxyanion hole, or sterically hinder the approach of the hydrolytic water.

Figure 8:
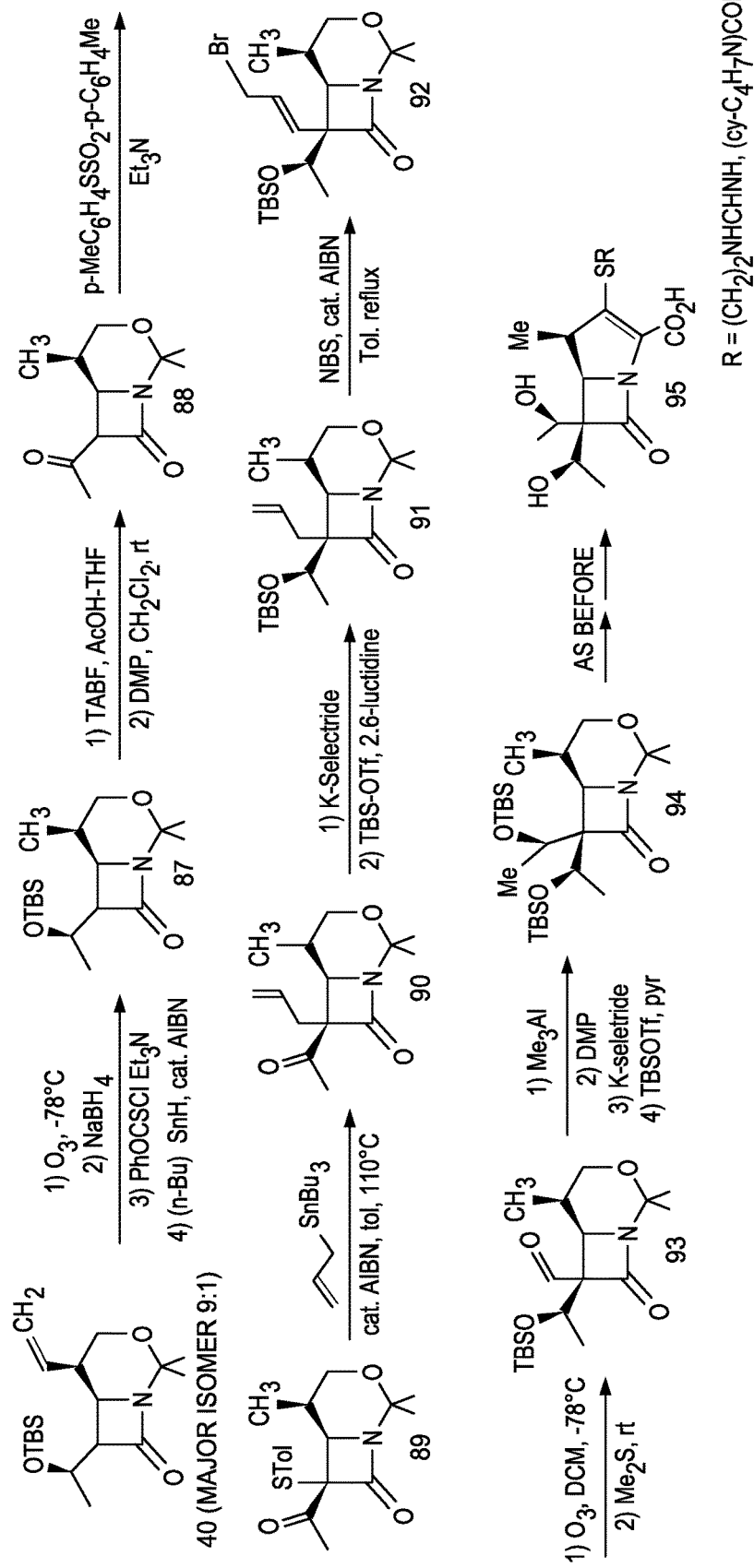
FIG. 8 is an image of the stereospecific synthesis of 6,6-disubstituted carbapenems having a C6α-((1'R)-hydroxyethyl) substituent.

FIG. 8 is an image of the stereospecific synthesis of 6,6-disubstituted carbapenems having a C6α-((1'R)-hydroxyethyl) substituent.

The present invention also provides a compound of formula I

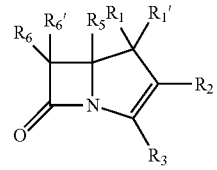

wherein: R1, R1', R2, R3, R5, R6 and R6' are each independently hydrogen, hydroxyl, carbonyl, carboxylate, carboxyl, carboxamide, amine, imine, imide, (C1-C10)alkyl, (C1-C10)alkanoyl, (C3-C8)cycloalkyl, (C2-C10)alkenyl, (C2-C10)alkynyl, —COOR, —CONRR, cyano, —C(=O)R*, —OR*, —CH$_2$OCONHRR*R*, —CONHR*R*R*, —CH$_2$OCONHR*, —CH$_2$CH$_2$OCONHR*, —CH$_2$OCONHR*, —CH$_2$CONHR*, —CH$_2$CH$_2$CONHR*, —CH$_2$NR*R*, —CH$_2$CH$_2$NR*R*, —CH$_2$CO$_2$, —CO$_2$, —CH$_2$OH, —CH$_2$CH$_2$OH, —CH$_2$CH$_2$NHCNH, —CH$_2$CONR*R*, aryl, heteroaryl, aryl(C1-C10)alkyl, heteroaryl(C1-C10)alkyl, —CH$_2$R, —(CH$_2$)n oxazolidinyl, isoxazolidinyl, morpholinyl, —R*, sulfide, sulfinyl, —SR*, —S(O)nR*, —NR*R*, azido, or halo. The R* group may independently be hydrogen, halo, cyano, cyanato, (C1-C10) alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. Furthermore, any of the groups herein may be optionally substituted with 1, 2, or 3 Z; and each Z is independently halo, nitro, cyano, hydroxy, (C1-C10)alkyl, (C3-C8)cycloalkyl, (C1-C10)alkoxy, (C,-C10)alkanoyl, (C2-C10)alkanoyloxy, trifluoromethyl, aryl, aryloxy, heteroaryl, or —SRn, wherein Rn is hydrogen, (C1-C10)alkyl, (C3-C8)

cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, (C1-C10)alkyl, (C3-C8)cycloalkyl, (C1-C10)alkoxy, (C1-C10)alkanoyl, (C2-C10)alkanoyloxy, and trifluoromethyl; or a pharmaceutically acceptable salt thereof.

For example, the present invention also provides a compound of the formula:

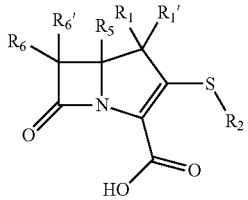

| | R1 | R1' | R2 | R5 | R6 | R6' |
|---|---|---|---|---|---|---|
| 1 | —CH$_2$OH | —CH$_3$ | —(CH$_2$)$_2$NHCHNH | —H | —CHOHCH$_3$ | —H |
| 2 | —CH$_2$OCONHR$_3$* | —CH$_3$ | —(CH$_2$)$_2$NHCHNH | —H | —CHOHCH$_3$ | —H |
| 3 | —CONHR$_3$* | —CH$_3$ | —(CH$_2$)$_2$NHCHNH | —H | —CHOHCH$_3$ | —H |
| 4 | —CO$_2$H | —CH$_3$ | —(CH$_2$)$_2$NHCHNH | —H | —CHOHCH$_3$ | —H |
| 5 | —CH$_2$OH | —CH$_3$ | —(cy-C$_4$H$_7$N)CONMe$_2$ | —H | —CHOHCH$_3$ | —H |
| 6 | —CH$_2$OCONHR$_3$* | —CH$_3$ | —(cy-C$_4$H$_7$N)CONMe$_2$ | —H | —CHOHCH$_3$ | —H |
| 7 | —CONHR$_3$* | —CH$_3$ | —(cy-C$_4$H$_7$N)CONMe$_2$ | —H | —CHOHCH$_3$ | —H |
| 8 | —CO$_2$H | —CH$_3$ | —(cy-C$_4$H$_7$N)CONMe$_2$ | —H | —CHOHCH$_3$ | —H |
| 9 | —CH$_2$OH | —H | —(CH$_2$)$_2$NHCHNH | —H | —CHOHCH$_3$ | —H |
| 10 | —CH$_2$OCONHR$_3$* | —H | —(CH$_2$)$_2$NHCHNH | —H | —CHOHCH$_3$ | —H |
| 11 | —CONHR$_3$* | —H | —(CH$_2$)$_2$NHCHNH | —H | —CHOHCH$_3$ | —H |
| 12 | —CO$_2$H | —H | —(CH$_2$)$_2$NHCHNH | —H | —CHOHCH$_3$ | —H |
| 13 | —CH$_2$OH | —H | —(cy-C$_4$H$_7$N)CONMe$_2$ | —H | —CHOHCH$_3$ | —H |
| 14 | —CH$_2$OCONHR$_3$* | —H | —(cy-C$_4$H$_7$N)CONMe$_2$ | —H | —CHOHCH$_3$ | —H |
| 15 | —CONHR$_3$* | —H | —(cy-C$_4$H$_7$N)CONMe$_2$ | —H | —CHOHCH$_3$ | —H |
| 16 | —CO$_2$H | —H | —(cy-C$_4$H$_7$N)CONMe$_2$ | —H | —CHOHCH$_3$ | —H |

The R* group may independently be hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. Furthermore, any of the groups herein may be optionally substituted with 1, 2, or 3 Z; and each Z is independently halo, nitro, cyano, hydroxy, (C1-C10)alkyl, (C3-C8)cycloalkyl, (C1-C10)alkoxy, (C,-C10)alkanoyl, (C2-C10)alkanoyloxy, trifluoromethyl, aryl, aryloxy, heteroaryl, or —SRn, wherein Rn is hydrogen, (C1-C10)alkyl, (C3-C8)cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, (C1-C10)alkyl, (C3-C8)cycloalkyl, (C1-C10)alkoxy, (C1-C10)alkanoyl, (C2-C10)alkanoyloxy, and trifluoromethyl; or a pharmaceutically acceptable salt thereof.

For example, the present invention also provides a compound of the formula:

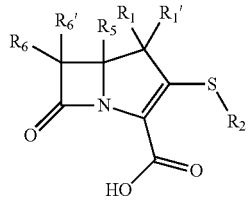

| | R1 | R1' | R2 | R5 | R6 | R6' |
|---|---|---|---|---|---|---|
| 17 | —R* | —CH$_2$OH | —(CH$_2$)$_2$NHCHNH | —H | —CHOHCH$_3$ | —H |
| 18 | —H | —CH$_2$OH | —(CH$_2$)$_2$NHCHNH | —H | —CHOHCH$_3$ | —H |
| 19 | —CH$_3$ | —CH$_2$OH | —(CH$_2$)$_2$NHCHNH | —H | —CHOHCH$_3$ | —H |
| 20 | —CH$_2$OH | —CH$_2$OH | —(CH$_2$)$_2$NHCHNH | —H | —CHOHCH$_3$ | —H |
| 21 | —CH$_2$OCONHR* | —CH$_2$OH | —(CH$_2$)$_2$NHCHNH | —H | —CHOHCH$_3$ | —H |
| 22 | —CONHR* | —CH$_2$OH | —(CH$_2$)$_2$NHCHNH | —H | —CHOHCH$_3$ | —H |
| 23 | —R* | —CH$_2$CH$_2$OH | —(CH$_2$)$_2$NHCHNH | —H | —CHOHCH$_3$ | —H |
| 24 | —H | —CH$_2$CH$_2$OH | —(CH$_2$)$_2$NHCHNH | —H | —CHOHCH$_3$ | —H |
| 25 | —CH$_3$ | —CH$_2$CH$_2$OH | —(CH$_2$)$_2$NHCHNH | —H | —CHOHCH$_3$ | —H |

-continued

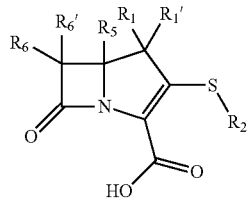

| | R1 | R1' | R2 | R5 | R6 | R6' |
|---|---|---|---|---|---|---|
| 26 | —CH₂OH | —CH₂CH₂OH | —(CH₂)₂NHCHNH | —H | —CHOHCH₃ | —H |
| 27 | —CH₂OCONHR* | —CH₂CH₂OH | —(CH₂)₂NHCHNH | —H | —CHOHCH₃ | —H |
| 28 | —CONHR* | —CH₂CH₂OH | —(CH₂)₂NHCHNH | —H | —CHOHCH₃ | —H |
| 29 | —R* | —CH₂OH | —(cy-C₄H₇N)CONMe₂ | —H | —CHOHCH₃ | —H |
| 30 | —H | —CH₂OH | —(cy-C₄H₇N)CONMe₂ | —H | —CHOHCH₃ | —H |
| 31 | —CH₃ | —CH₂OH | —(cy-C₄H₇N)CONMe₂ | —H | —CHOHCH₃ | —H |
| 32 | —CH₂OH | —CH₂OH | —(cy-C₄H₇N)CONMe₂ | —H | —CHOHCH₃ | —H |
| 33 | —CH₂OCONHR* | —CH₂OH | —(cy-C₄H₇N)CONMe₂ | —H | —CHOHCH₃ | —H |
| 34 | —CONHR* | —CH₂OH | —(cy-C₄H₇N)CONMe₂ | —H | —CHOHCH₃ | —H |
| 35 | —R* | —CH₂CH₂OH | —(cy-C₄H₇N)CONMe₂ | —H | —CHOHCH₃ | —H |
| 36 | —H | —CH₂CH₂OH | —(cy-C₄H₇N)CONMe₂ | —H | —CHOHCH₃ | —H |
| 37 | —CH₃ | —CH₂CH₂OH | —(cy-C₄H₇N)CONMe₂ | —H | —CHOHCH₃ | —H |
| 38 | —CH₂OH | —CH₂CH₂OH | —(cy-C₄H₇N)CONMe₂ | —H | —CHOHCH₃ | —H |
| 39 | —CH₂OCONHR* | —CH₂CH₂OH | —(cy-C₄H₇N)CONMe₂ | —H | —CHOHCH₃ | —H |
| 40 | —CONHR* | —CH₂CH₂OH | —(cy-C₄H₇N)CONMe₂ | —H | —CHOHCH₃ | —H |

The R* group may independently be hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. Furthermore, any of the groups herein may be optionally substituted with 1, 2, or 3 Z; and each Z is independently halo, nitro, cyano, hydroxy, (C1-C10)alkyl, (C3-C8)cycloalkyl, (C1-C10)alkoxy, (C,-C10)alkanoyl, (C2-C10)alkanoyloxy, trifluoromethyl, aryl, aryloxy, heteroaryl, or —SRn, wherein Rn is hydrogen, (C1-C10)alkyl, (C3-C8)cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, (C1-C10)alkyl, (C3-C8)cycloalkyl, (C1-C10)alkoxy, (C1-C10)alkanoyl, (C2-C10)alkanoyloxy, and trifluoromethyl; or a pharmaceutically acceptable salt thereof.

For example, the present invention also provides a compound of the formula:

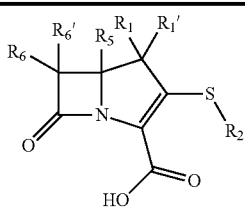

| | R1 | R1' | R2 | R5 | R6 | R6' |
|---|---|---|---|---|---|---|
| 41 | R* | —CH₂OCONHR* | R2 | —H | —CHOHCH₃ | —H |
| 42 | R* | —CH₂CH₂OCONHR* | R2 | —H | —CHOHCH₃ | —H |
| 43 | R* | —CH₂CONHR* | R2 | —H | —CHOHCH₃ | —H |
| 44 | R* | —CH₂CH₂CONHR* | R2 | —H | —CHOHCH₃ | —H |
| 45 | R* | —CH₂CH₂OH | R2 | —H | —CHOHCH₃ | —H |
| 46 | R* | —CH₂CH₂CH₂OH | R2 | —H | —CHOHCH₃ | —H |

-continued

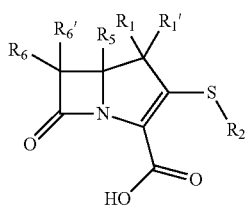

| | R1 | R1' | R2 | R5 | R6 | R6' |
|---|---|---|---|---|---|---|
| 47 | R* | —CH₂NHR* | R2 | —H | —CHOHCH₃ | —H |
| 48 | R* | —CH₂CH₂NHR* | R2 | —H | —CHOHCH₃ | —H |

The R2 and R* groups may independently be hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. Furthermore, any of the groups herein may be optionally substituted with 1, 2, or 3 Z; and each Z is independently halo, nitro, cyano, hydroxy, (C1-C10)alkyl, (C3-C8)cycloalkyl, (C1-C10)alkoxy, (C,-C10)alkanoyl, (C2-C10)alkanoyloxy, trifluoromethyl, aryl, aryloxy, heteroaryl, or —SRn, wherein Rn is hydrogen, (C1-C10)alkyl, (C3-C8)cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, (C1-C10)alkyl, (C3-C8)cycloalkyl, (C1-C10)alkoxy, (C1-C10)alkanoyl, (C2-C10)alkanoyloxy, and trifluoromethyl; or a pharmaceutically acceptable salt thereof.

For example, the present invention also provides a compound of the formula:

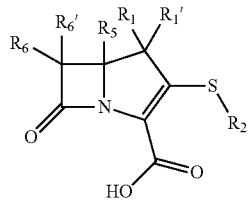

| | R1 | R1' | R2 | R5 | R6 | R6' |
|---|---|---|---|---|---|---|
| 49 | R* | —CH$_2$OCONHR* | —(CH$_2$)$_2$NHCHNH | —H | —CHOHCH$_3$ | —H |
| 50 | R* | —CH$_2$CH$_2$OCONHR* | —(CH$_2$)$_2$NHCHNH | —H | —CHOHCH$_3$ | —H |
| 51 | R* | —CH$_2$CONHR* | —(CH$_2$)$_2$NHCHNH | —H | —CHOHCH$_3$ | —H |
| 52 | R* | —CH$_2$CH$_2$CONHR* | —(CH$_2$)$_2$NHCHNH | —H | —CHOHCH$_3$ | —H |
| 53 | R* | —CH$_2$CH$_2$OH | —(CH$_2$)$_2$NHCHNH | —H | —CHOHCH$_3$ | —H |
| 54 | R* | —CH$_2$CH$_2$CH$_2$OH | —(CH$_2$)$_2$NHCHNH | —H | —CHOHCH$_3$ | —H |
| 55 | R* | —CH$_2$NHR* | —(CH$_2$)$_2$NHCHNH | —H | —CHOHCH$_3$ | —H |
| 56 | R* | —CH$_2$CH$_2$NHR* | —(CH$_2$)$_2$NHCHNH | —H | —CHOHCH$_3$ | —H |

The R* group may independently be hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. Furthermore, any of the groups herein may be optionally substituted with 1, 2, or 3 Z; and each Z is independently halo, nitro, cyano, hydroxy, (C1-C10)alkyl, (C3-C8)cycloalkyl, (C1-C10)alkoxy, (C,-C10) alkanoyl, (C2-C10)alkanoyloxy, trifluoromethyl, aryl, aryloxy, heteroaryl, or —SRn, wherein Rn is hydrogen, (C1-C10)alkyl, (C3-C8)cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, (C1-C10)alkyl, (C3-C8)cycloalkyl, (C1-C10)alkoxy, (C1-C10)alkanoyl, (C2-C10)alkanoyloxy, and trifluoromethyl; or a pharmaceutically acceptable salt thereof.

For example, the present invention also provides a compound of the formula:

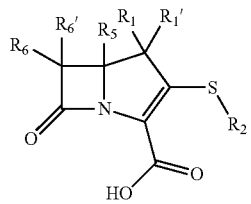

| | R1 | R1' | R2 | R5 | R6' | R6 |
|---|---|---|---|---|---|---|
| 57 | R* | —CH$_2$OCONHR* | —(cy-C$_4$H$_7$N)CONMe$_2$ | —H | —H | —CHOHCH$_3$ |
| 58 | R* | —CH$_2$CH$_2$OCONHR* | —(cy-C$_4$H$_7$N)CONMe$_2$ | —H | —H | —CHOHCH$_3$ |
| 59 | R* | —CH$_2$CONHR* | —(cy-C$_4$H$_7$N)CONMe$_2$ | —H | —H | —CHOHCH$_3$ |
| 60 | R* | —CH$_2$CH$_2$CONHR* | —(cy-C$_4$H$_7$N)CONMe$_2$ | —H | —H | —CHOHCH$_3$ |
| 61 | R* | —CH$_2$CH$_2$OH | —(cy-C$_4$H$_7$N)CONMe$_2$ | —H | —H | —CHOHCH$_3$ |
| 62 | R* | —CH$_2$CH$_2$CH$_2$OH | —(cy-C$_4$H$_7$N)CONMe$_2$ | —H | —H | —CHOHCH$_3$ |
| 63 | R* | —CH$_2$NHR* | —(cy-C$_4$H$_7$N)CONMe$_2$ | —H | —H | —CHOHCH$_3$ |
| 64 | R* | —CH$_2$CH$_2$NHR* | —(cy-C$_4$H$_7$N)CONMe$_2$ | —H | —H | —CHOHCH$_3$ |

The R* group may independently be hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. Furthermore, any of the groups herein may be optionally substituted with 1, 2, or 3 Z; and each Z is independently halo, nitro, cyano, hydroxy, (C1-C10)alkyl, (C3-C8)cycloalkyl, (C1-C10)alkoxy, (C,-C10)alkanoyl, (C2-C10)alkanoyloxy, trifluoromethyl, aryl, aryloxy, heteroaryl, or —SRn, wherein Rn is hydrogen, (C1-C10)alkyl, (C3-C8)cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, (C1-C10)alkyl, (C3-C8)cycloalkyl, (C1-C10)alkoxy, (C1-C10)alkanoyl, (C2-C10)alkanoyloxy, and trifluoromethyl; or a pharmaceutically acceptable salt thereof.

For example, the present invention also provides a compound of the formula:

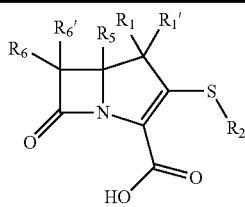

| | R1 | R1' | R2 | R5 | R6 | R6' |
|---|---|---|---|---|---|---|
| 65 | —H | —H | R2 | —CH$_3$ | —CHOHCH$_3$ | —H |
| 66 | —H | —H | R2 | —CH$_2$NHR* | —CHOHCH$_3$ | —H |
| 67 | —H | —H | R2 | —CH$_2$OCONHR* | —CHOHCH$_3$ | —H |
| 68 | —H | —H | R2 | —CH$_2$COCONHR* | —CHOHCH$_3$ | —H |

The R* group may independently be hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. Furthermore, any of the groups herein may be optionally substituted with 1, 2, or 3 Z; and each Z is independently halo, nitro, cyano, hydroxy, (C1-C10)alkyl, (C3-C8)cycloalkyl, (C1-C10)alkoxy, (C,-C10)alkanoyl, (C2-C10)alkanoyloxy, trifluoromethyl, aryl, aryloxy, heteroaryl, or —SRn, wherein Rn is hydrogen, (C1-C10)alkyl, (C3-C8)cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, (C1-C10)alkyl, (C3-C8)cycloalkyl, (C1-C10)alkoxy, (C1-C10)alkanoyl, (C2-C10)alkanoyloxy, and trifluoromethyl; or a pharmaceutically acceptable salt thereof.

For example, the present invention also provides a compound of the formula:

| | R1 | R1' | R2 | R5 | R6 | R6' |
|---|---|---|---|---|---|---|
| 69 | —H | —H | —(CH$_2$)$_2$NHCHNH | —CH$_3$ | —CHOHCH$_3$ | —H |
| 70 | —H | —H | —(CH$_2$)$_2$NHCHNH | —CH$_2$NHR* | —CHOHCH$_3$ | —H |
| 71 | —H | —H | —(CH$_2$)$_2$NHCHNH | —CH$_2$OCONHR* | —CHOHCH$_3$ | —H |
| 72 | —H | —H | —(cy-C$_4$H$_7$N)CONMe$_2$ | —CH$_3$ | —CHOHCH$_3$ | —H |
| 73 | —H | —H | —(cy-C$_4$H$_7$N)CONMe$_2$ | —CH$_2$NHR* | —CHOHCH$_3$ | —H |
| 74 | —H | —H | —(cy-C$_4$H$_7$N)CONMe$_2$ | —CH$_2$OCONHR* | —CHOHCH$_3$ | —H |

The R* group may independently be hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. Furthermore, any of the groups herein may be optionally substituted with 1, 2, or 3 Z; and each Z is independently halo, nitro, cyano, hydroxy, (C1-C10)alkyl, (C3-C8)cycloalkyl, (C1-C10)alkoxy, (C,-C10) alkanoyl, (C2-C10)alkanoyloxy, trifluoromethyl, aryl, aryloxy, heteroaryl, or —SRn, wherein Rn is hydrogen, (C1-C10)alkyl, (C3-C8)cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, (C1-C10)alkyl, (C3-C8)cycloalkyl, (C1-C10)alkoxy, (C1-C10)alkanoyl, (C2-C10)alkanoyloxy, and trifluoromethyl; or a pharmaceutically acceptable salt thereof.

For example, the present invention also provides a compound of the formula:

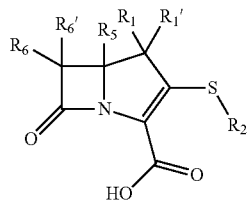

| | R1 | R1' | R2 | R5 | R6 | R6' |
|---|---|---|---|---|---|---|
| 75 | —H | —CH$_3$ | —(CH$_2$)$_2$NHCHNH | —H | —CHOHCH$_3$ | —CHOHCH$_3$ |
| 76 | —H | —CH$_3$ | —(cy-C$_4$H$_7$N)CONMe$_2$ | —H | —CHOHCH$_3$ | —CHOHCH$_3$ |
| 77 | —H | —CH$_3$ | (cy-C$_4$H$_7$N)CONMe$_2$ | —H | —CHOHCH$_3$ | —CHOHCH$_3$ |
| 78 | —H | —CH$_3$ | (cy-C$_4$H$_7$N)CONMe$_2$ | —H | —CHOHCH$_3$ | —CHOHCH$_3$ |

The R* group may independently be hydrogen, halo, cyano, cyanato, (C1-C10)alkyl, (C3-C8)cycloalkyl, (C2-C10)alkenyl, (C2-C10)alkynyl, (C1-C10)alkanoyl, aryl, benzyl, phenethyl, heteroaryl, sulfide, sulfinyl, oxazolidinyl, isoxazolidinyl, or morpholinyl; together with the nitrogen may form a triazolyl, imidazolyl, oxazolidinyl, isoxazolidinyl, pyrrolyl, morpholino, piperidino, pyrrolidino, pyrazolyl, indolyl, or tetrazolyl. Furthermore, any of the groups herein may be optionally substituted with 1, 2, or 3 Z; and each Z is independently halo, nitro, cyano, hydroxy, (C1-C10)alkyl, (C3-C8)cycloalkyl, (C1-C10)alkoxy, (C,-C10)alkanoyl, (C2-C10)alkanoyloxy, trifluoromethyl, aryl, aryloxy, heteroaryl, or —SRn, wherein Rn is hydrogen, (C1-C10)alkyl, (C3-C8)cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, (C1-C10)alkyl, (C3-C8)cycloalkyl, (C1-C10)alkoxy, (C1-C10)alkanoyl, (C2-C10)alkanoyloxy, and trifluoromethyl; or a pharmaceutically acceptable salt thereof.

As used herein R2 may be a pharmaceutically acceptable group which is bonded to the remaining part of the molecule by an oxygen-carbon single bond or a nitrogen-carbon single bond, and which is selected from the group comprising substituted or unsubstituted: alkoxy, alkenyloxy, alkinyloxy, cycloalkoxy, N-heterocyclyl, heterocyclyloxy, heterocyclylcarbonyloxy, heterocyclylthiocarbonyloxy, acyloxy, thioacyloxy, alkoxycarbonyloxy, carbamoyloxy, thiocarbamoyloxy, heterocyclyloxycarbonyloxy, heterocycly loxythiocarbony loxy, N-heterocyclycarbamoyloxy, N-heterocyclylthiocarbamoyloxy, heterocyclylcarbonylamino, heterocyclylthiocarbonylamino, heterocyclyloxycarbonylamino, acylamino, alkoxycarbonylamino, alkoxythiocarbonylamino, thioacyclamino, N-heterocyclylcarbamoylamino, N-heterocyclylthiocarbamoylamino, carbamoylamino, thiocarbamoylamino, imidoylamino, guanidino, N-heterocycly 1-alkoxycarbonylamino, N-heterocycly 1-alkylthiocarbonylamino and N-sulfonylamino where the foregoing alkyl, alkenyl, alkinyl, acyl, thioacyl or imidoyl molecule parts contain 1 to 6 carbon atoms and the heterocyclyl moiety is monocyclic or bicyclic and contains 3 to 10 ring atoms, of which one or more are selected from the series comprising: oxygen, sulphur and nitrogen and where the substituents of the above mentioned groups R3 may be: alkyl, acyl, thioacyl, heterocyclyl, hydroxyl, hydroxyalkyl, alkoxy, hydroxyalkoxy, aminoalkoxy, amidinoalkoxy, guanidinoalkoxy, acyloxy, heterocyclyloxy, alkylheterocyclyloxy, hydroxyalkylheterocyclyloxy, aminoalkylheterocyclyloxy, carbamoyl, alkylcarbamoyl, dialkylcarbamoyl, carbamoyloxy, alkylcarbamoyloxy, dialkylcarbamoyloxy, thiocarbamoyl, alkylthiocarbamoyl, dialkylthiocarbamoyl, thiocarbamoyloxy, alkylthiocarbamoyloxy, dialkylthiocarbamoyloxy, mercapto, alkylthio, hydroxyalkylthio, aminoalkylthio, monoalkylaminoalkylthio, dialkylaminoalkylthio, amidinoalkylthio, acylthio, heterocyclylthio, alkylheterocyclylthio, hydroxyalkylheterocyclylthio, aminoalkylheterocyclylthio, carbamoylthio, monoalkylcarbamoylthio, dialkylcarbamoylthio, thiocarbamoylthio, alkylthiocarbamoylthio, dialkylcarbamoylthio, amino, monoalkylamino, hydroxyalkylamino, aminoalkylamino, dialkylamino, oxo, oximino, or alkylimino, imidoylamino, alkylimidoylamino, dialkylimidoylamino, tetraalkylammonium, cycloalkylamino, heterocyclylamino, alkylheterocyclylamino, heterocyclylcarbonylamino, alkylheterocyclylcarbonylamino, acylamino, amidino, monoalkylamidino, dialkylamidino, guanidino, alkylguanidino, dialkylguanidino, carbamoylamino, thiocarbamoylamino, alkylcarbamoylamino, thiocarbamoylamino, alkylthiocarbamoylamino, nitro, chloro, bromo, fluoro, iodo, azido, cyano, alkylsulphinyl, alkylsulphonyl, sulphonamido, sulphamoyloxy, alkylsulphamoyloxy, alkylsulphonyloxy or sulpha, sulphoxy, carboxamido, N-monoalkylcarboxamido, N,Ndialkylcarboxamido or carboxy, where the substituents, independently of one another, occur once or several times and their alkyl moiety contains 1 to 6 carbon atoms, and where the heterocyclic moiety is monocyclic or bicyclic and contains 3 to 10 ring atoms, of which one or more are selected from the series comprising: oxygen, sulphur and nitrogen. R2 may be a {2-[(iminomethyl)amino]ethyl}; [5-(dimethylcarbamoyl)pyrrolidin-2-yl]; [(3S,5S)-5-[(3-carboxyphenyl)carbamoyl]pyrrolidin-3-yl]; [(3S,5S)-5-[(sulfamoylamino)methyl]pyrrolidin-3-yl]; {[(3S)-1-ethanimidoylpyrrolidin-3-yl]; (6,7-dihydro-5H-pyrazolo[1,2-a][1,2,4]triazol-8-ium-6-ylsulfanyl).

The present invention provides a carbapenem compound having the formula

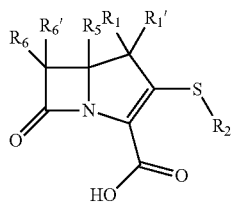

It is understood that the compositions of the instant application will have substitutions at one or more locations (e.g., R1, R1', R2, R5, R6, and/or R6'). For example, the core carbapenem may be a imipenem, meropenem, ertapenem doripenem, panipenem, or biapenem with substitutions at R1, R1', R5, R6, and/or R6' as discussed herein. As such, the core composition may have substitutions at R2 as seen in U.S. Pat. Nos. 8,148,520, 7,468,364 and U.S. Patent Application Publication No. 2010/0173887 and 2009/0312539 (each of which is incorporated herein by reference) as non-limiting examples.

It will be appreciated by those skilled in the art that compounds of the invention having one or more chiral centers may exist and be isolated as optically active and racemic forms. Some compounds may exhibit polymorphism. It is to be understood that the present invention encompasses any racemic, optically-active, polymorphic, or stereoisomeric form, or mixtures thereof, of a compound of the invention, that possesses the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine β-lactamase inhibitory activity using the tests described herein, or using other tests which are well known in the art.

As used herein, the term halo denotes fluoro, chloro, bromo, or iodo.

As used herein, the terms Alkyl, alkoxy, alkenyl, alkynyl, etc. denote both straight and branched groups.

As used herein, the term Aryl denotes a phenyl radical or an ortho-fused bicyclic carbocyclic radical having about four to ten ring atoms in which at least one ring is aromatic.

As used herein, the term heteroaryl encompasses a radical attached via a ring carbon of a monocyclic aromatic ring containing four or ten ring atoms consisting of carbon and one to four heteroatoms each selected from the group consisting of non-peroxide oxygen, sulfur, and N(X) wherein each X is absent or is H, O, (C1-C4)alkyl, phenyl or benzyl, as well as a radical of an ortho-fused bicyclic heterocycle of about four to ten ring atoms derived therefrom, particularly a benz-derivative or one derived by fusing a propylene, trimethylene, or tetramethylene diradical thereto.

For example, (C1-C10) alkyl can be methyl, ethyl, propyl, isopropyl, butyl, iso-butyl, sec-butyl, pentyl, 3-pentyl, hexyl, heptyl, octyl, nonyl or decyl; (C3-C8)cycloalkyl can be cyclopropyl, cyclobutyl, cyclopentyl, cyclohexyl, cycloheptyl, or cyclooctyl; (C1-C10) alkoxy can be methoxy, ethoxy, propoxy, isopropoxy, butoxy, iso-butoxy, sec-butoxy, pentoxy, 3-pentoxy, hexyloxy, heptyloxy, octyloxy, nonyloxy, or decyloxy; (C2-C10) alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8ecenyl, or 9-decenyl; (C2-C10) alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, or 9-decynyl; (C1-C10) alkanoyl can be acetyl, propanoyl, butanoyl, isobutanoyl, pentanoyl, hexanoyl, heptanoyl, octanoyl, nonanoyl, or decanoyl; and (C2-C10) alkanoyloxy can be acetoxy, propanoyloxy, butanoyloxy, isobutanoyloxy, pentanoyloxy, hexanoyloxy, heptanoyloxy, octanoyloxy, nonanoyloxy, or decanoyloxy.

For example, "aryl" can be phenyl, indenyl, or naphthyl. Specifically, "heteroaryl" can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), thiadiazolyl, thiatriazolyl, oxadiazolyl, or quinolyl (or its N-oxide). "Heteroaryl" can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide). More specifically, heteroaryl can be pyridyl.

It is noted that many of the starting materials employed in the synthetic methods described above are commercially available or are reported in the scientific literature. It is also noted that it may be desirable to optionally use a protecting group during all or portions of the above described synthetic procedures. Such protecting groups and methods for their introduction and removal are well known in the art (see Greene, T. W.; Wutz, P. G. M. "Protecting Groups in Organic Synthesis," second edition, 1991, New York, John Wiley & Sons, Inc.).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, .alpha.-ketoglutarate, and .alpha.-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made. Salts of the present invention include mono-, di-, or tri-salt from a corresponding compound of the present invention.

The compositions disclosed herein can be formulated as pharmaceutical compositions and administered to a mammalian host, such as a human patient in a variety of forms adapted to a selected route of administration, i.e., by oral, parenteral, intravenous, intramuscular, topical, or subcutaneous routes.

The compositions of the present invention may be administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compositions may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compositions of the present invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compositions of the present invention can be determined by comparing their in vitro activity, and in vivo activity in animal models. Methods for extrapolating effective dosages in humans, mice, (and other animals) are known in the art; e.g., U.S. Pat. No. 4,938,949.

Generally, the concentration of the compositions of the present invention in a liquid composition, such as a lotion, will be from about 0.1-25 wt-%, preferably from about 0.5-10 wt-%. The concentration in a semi-solid or solid composition such as a gel or a powder will be about 0.1-25 wt-%, preferably 0.1-5 wt-%, preferably about 0.5-2.5 wt-%. Single dosages for injection, infusion or ingestion will generally vary between 50-1500 mg, and may be administered, i.e., 1-3 times daily, to yield levels of about 0.5-50 mg/kg, for adults.

The invention provides a pharmaceutical composition of an effective amount of a compound as described hereinabove; or a pharmaceutically acceptable salt thereof; and a pharmaceutically acceptable carrier. The invention also provides a pharmaceutical composition comprising an effective amount of a compound as described hereinabove or a pharmaceutically acceptable salt thereof; a β-lactam antibiotic; and a pharmaceutically acceptable carrier. Any β-Lactam antibiotic is suitable for use in the pharmaceutical composition of the invention. β-Lactam antibiotics which are well known in the art include those disclosed by R. B. Morin and M. Gorin, M. Eds.; Academic Press, New York, 1982; vol. 1-3. For example, β-Lactam antibiotics, suitable for use in the pharmaceutical composition of the invention, include β-lactam antibiotics which are preferentially deactivated by Class A and Class C β-lactamase enzymes, for example, amoxicillin, piperacillin, ampicillin, ceftizoxime, cefotaxime, cefuroxime, cephalexin, cefaclor, cephaloridine, and ceftazidime.

Because compounds of the invention inhibit β-lactamase enzymes, they may also be useful to increase the effectiveness of β-lactam antibiotics which are degraded by such enzymes. Accordingly, the invention provides a method comprising enhancing (increasing by a detectable amount) the activity of a β-lactam antibiotic, by administering the β-lactam antibiotic to a mammal (preferably a human) in need thereof, in combination with an effective amount of a composition of the present invention or a pharmaceutically acceptable salt thereof.

The invention also provides a method comprising treating a β-lactam resistant bacterial infection in a mammal, by administering an effective amount of a β-lactam antibiotic in combination with an effective β-lactamase inhibiting amount of a composition of the present invention or a pharmaceutically acceptable salt thereof.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A composition comprising a carbapenem compound having the formula:

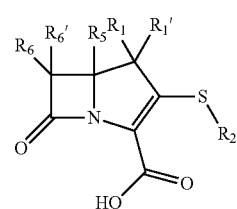

or enantiomers or diastereoisomers thereof,
wherein R1 and R1' are independently selected from —H, —CH$_2$CH$_2$OH, —CHOHCH$_3$, —CH$_2$NHR*, —CH$_2$OCONHR* and —CO$_2$H;
wherein R5 is selected from —CH$_2$NHR*, —CH$_2$OCONHR* and —CH$_2$COCONHR*;
wherein R6 and R6' are independently selected from —H and —CHOHCH$_3$;

wherein R* is hydrogen; and
wherein R2 is
{2-[(iminomethyl)amino]ethyl}

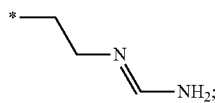

[5-(dimethylcarbamoyl) pyrrolidin-2-yl]

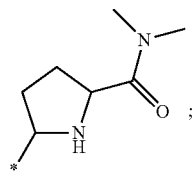 [SMILES: *C1CCC(C(=O)N(C)C)N1]

or
[(3S)-1-ethanimidoylpyrrolidin-3-yl]

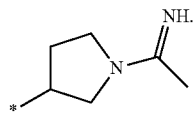

2. An antibacterial composition comprising
a carbapenem compound or its pharmaceutically acceptable salt as an active ingredient having the formula:

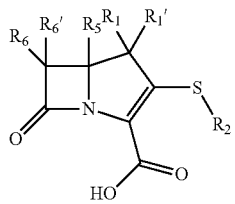

or enantiomers or diastereoisomers thereof,
wherein R1 and R1' are independently selected from —H, —CH$_2$CH$_2$OH, —CHOHCH$_3$, —CH$_2$NHR*, —CH$_2$OCONHR* and —CO$_2$H;
wherein R5 is selected from —CH$_2$NHR*, —CH$_2$OCONHR* and —CH$_2$COCONHR*;
wherein R6 and R6' are independently selected from —H and —CHOHCH$_3$;
wherein R* is hydrogen; and
wherein R2 is
{2-[(iminomethyl)amino]ethyl}

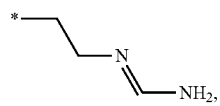

or
[5-(dimethylcarbamoyl) pyrrolidin-2-yl]

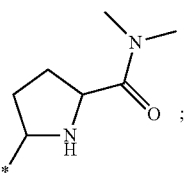 [SMILES: *C1CCC(C(=O)N(C)C)N1]

and a pharmaceutically acceptable carrier, excipient, binder or stabilizer.

* * * * *

UNITED STATES PATENT AND TRADEMARK OFFICE
CERTIFICATE OF CORRECTION

| | | |
|---|---|---|
| PATENT NO. | : 10,519,161 B2 | Page 1 of 1 |
| APPLICATION NO. | : 14/066367 | |
| DATED | : October 29, 2013 | |
| INVENTOR(S) | : John D. Buynak | |

It is certified that error appears in the above-identified patent and that said Letters Patent is hereby corrected as shown below:

In the Specification

In the STATEMENT OF FEDERALLY FUNDED RESEARCH, at Column 1, Line 17, the Contract No. 1R41AI102507-01 should be changed to AI102507.

Signed and Sealed this
Second Day of May, 2023

*Katherine Kelly Vidal*

Katherine Kelly Vidal
*Director of the United States Patent and Trademark Office*